(12) United States Patent
Srinivasan et al.

(10) Patent No.: US 8,877,501 B2
(45) Date of Patent: Nov. 4, 2014

(54) PRODUCTION OF ALKALOIDS BY LILIACEAE CELL CULTURE

(75) Inventors: Venkatesh Srinivasan, Sunnyvale, CA (US); Jennifer Alford, Ithaca, NY (US); Beth Slusar-Place, New York, NY (US); Charles Swindell, Merion, PA (US); Michael Horn, Noblesville, IN (US); Khisal Alvi, San Diego, CA (US); Gilbert Gorr, Freiburg (DE)

(73) Assignee: Phyton Holdings, LLC, Wilmington, DE (US)

( * ) Notice: Subject to any disclaimer, the term of this patent is extended or adjusted under 35 U.S.C. 154(b) by 0 days.

(21) Appl. No.: 13/378,962

(22) PCT Filed: Jun. 18, 2010

(86) PCT No.: PCT/US2010/039228
§ 371 (c)(1),
(2), (4) Date: Aug. 3, 2012

(87) PCT Pub. No.: WO2010/148338
PCT Pub. Date: Dec. 23, 2010

(65) Prior Publication Data
US 2012/0302754 A1    Nov. 29, 2012

Related U.S. Application Data

(60) Provisional application No. 61/218,178, filed on Jun. 18, 2009, provisional application No. 61/348,070, filed on May 25, 2010.

(51) Int. Cl.
C12N 5/00       (2006.01)
C12N 5/02       (2006.01)
C12P 17/18      (2006.01)

(52) U.S. Cl.
CPC .................................. *C12P 17/188* (2013.01)
USPC .............. 435/410; 435/53; 435/119; 435/420

(58) Field of Classification Search
USPC ................... 435/53, 119, 410, 420
See application file for complete search history.

(56) References Cited

FOREIGN PATENT DOCUMENTS

WO    WO 2008037732 A1 *  4/2008

OTHER PUBLICATIONS

Ma et al. "Development of in vitro Techniques for the Important Medicinal Plant *Veratrum californicum*," Planta Med 2006; 72: 1142-1148.*
Debnath et al. "Micropropagation: A Tool for the Production of High Quality Plant-based Medicines," Current Pharmaceutical Biotechnology, 2006, 7, pp. 33-49.*
Ziv, M. "Bioreactor Technology for Plant Micropropagation," Horticultural Reviews, vol. 24, 2000, pp. 1-30.*
Valluri, J. "Bioreactor Production of Secondary Metabolites from Cell Cultures of Periwinkle and Sandalwood," Methods in Molecular Biology, vol. 547, 2009, pp. 325-335.*

* cited by examiner

*Primary Examiner* — Susan McCormick Ewoldt
(74) *Attorney, Agent, or Firm* — Hunton & Williams LLP

(57) ABSTRACT

The present invention relates to the production of alkaloids from Liliaceae cell culture.

18 Claims, 11 Drawing Sheets

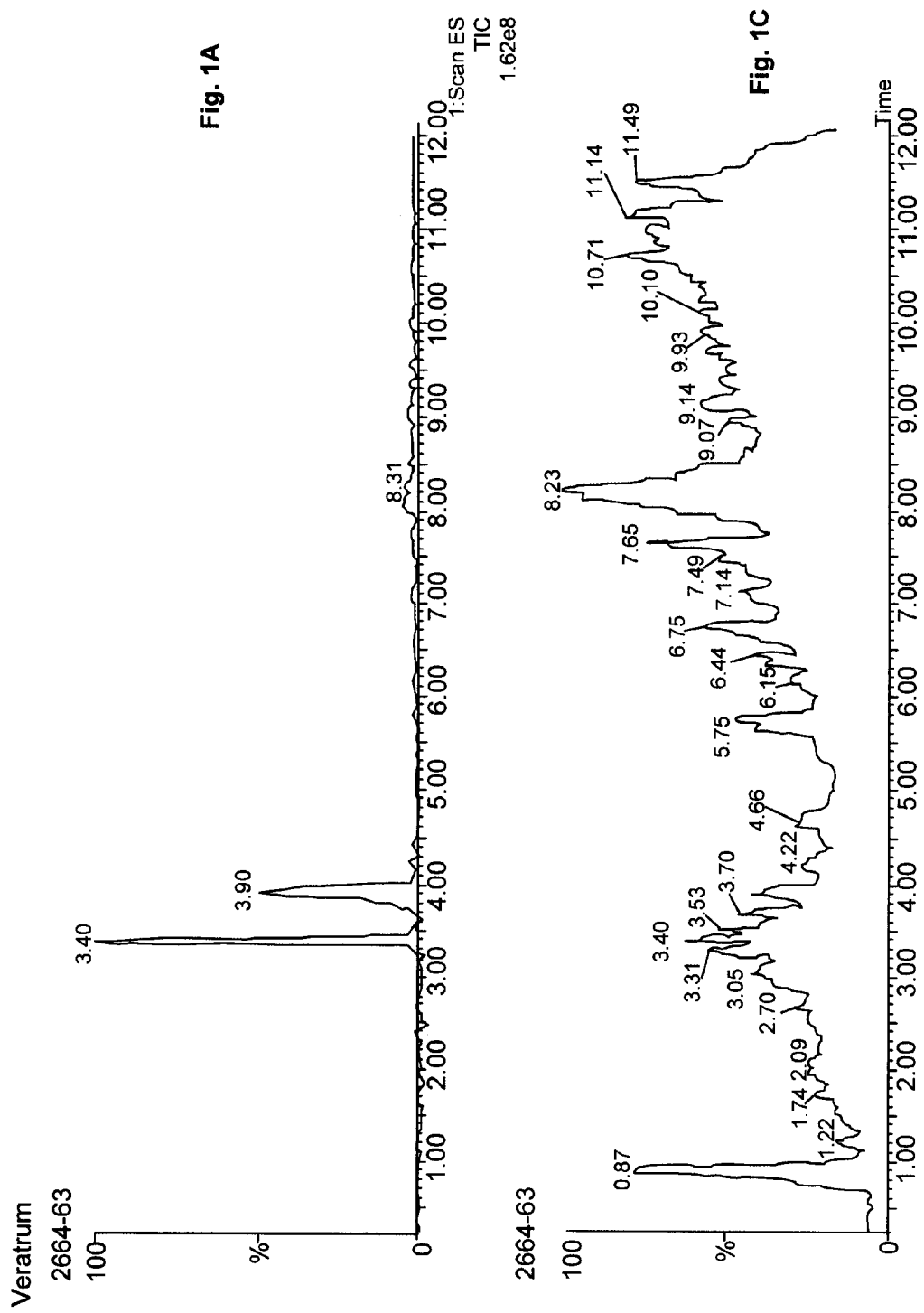

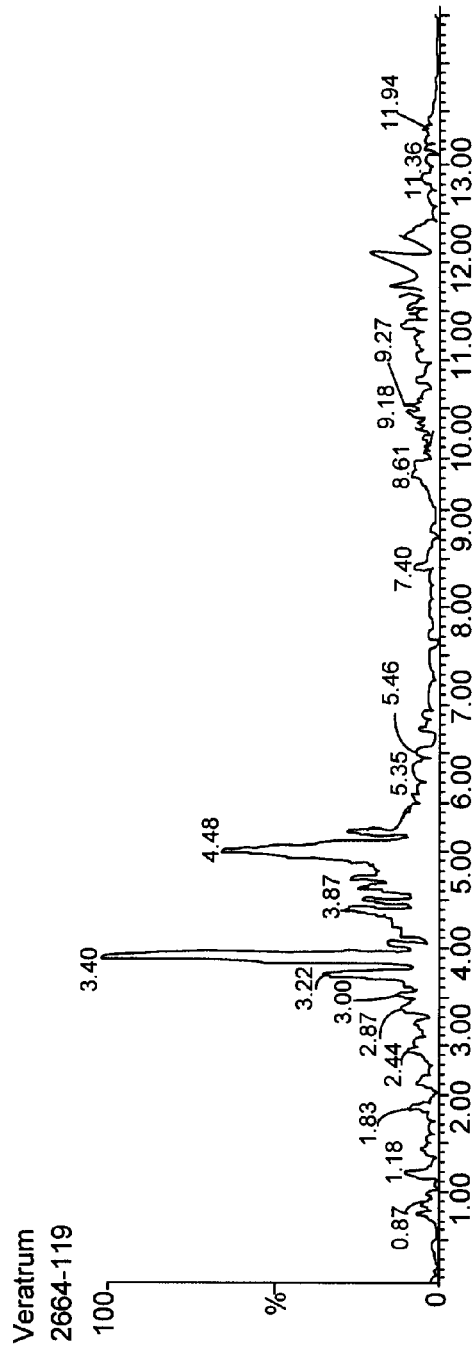
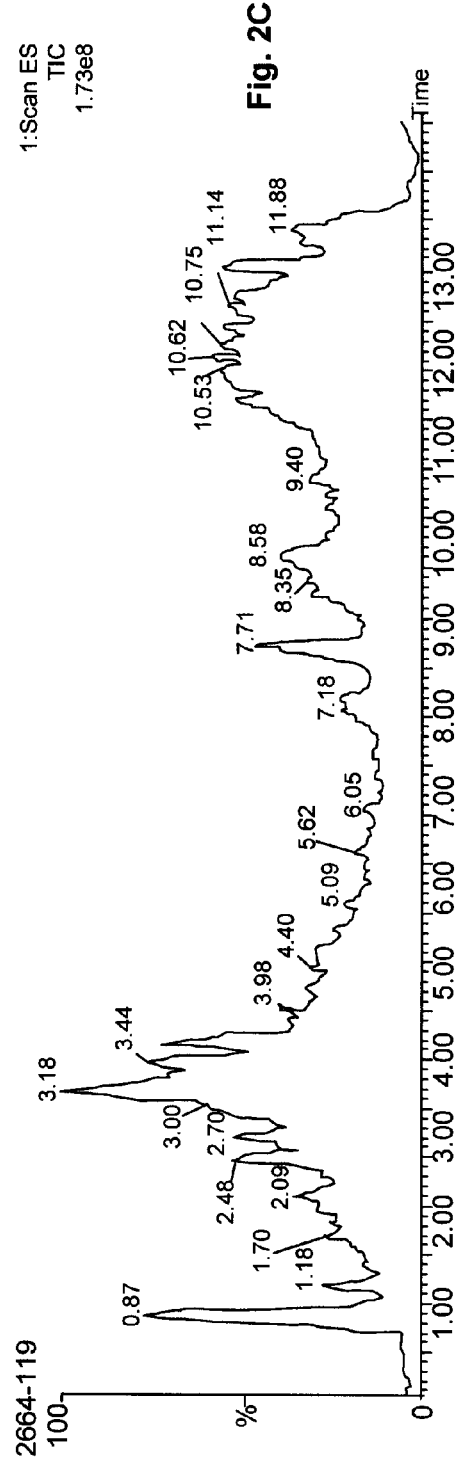
Fig. 2A
Fig. 2C

US 8,877,501 B2

PRODUCTION OF ALKALOIDS BY LILIACEAE CELL CULTURE

This application is a U.S. National Stage of International Application PCT/US2010/039228, filed Jun. 18, 2010, which claims priority to U.S. Provisional Application No. 61/218,178, filed Jun. 18, 2009, and U.S. Provisional Application No. 61/348,070, filed May 25, 2010, the contents of each are hereby incorporated by reference in their entirety.

FIELD OF THE INVENTION

The present invention relates to the production of alkaloids from Liliaceae cell culture.

BACKGROUND OF THE INVENTION

The Hedgehog (Hh) pathway plays a critical role in human embryogenesis and tissue differentiation, and thus, disruption of the Hh pathway is implicated in some birth defects as well as cancers. Small molecules can be used to activate or block the Hh pathway, e.g., by targeting Patched, a protein of the Hh pathway that inhibits cell division, or Smoothened, a protein of the Hh pathway that promotes cell division. For example, the alkaloid cyclopamine, which is found in plants of the *Veratrum* genus of the Liliaceae family, can block the Hh pathway by targeting Smoothened, thus inhibiting cell growth. Cyclopamine and other alkaloids of the *Veratrum* superfamily have been identified as potential therapeutic agents to treat diseases in which the Hh pathway is implicated. Likewise, biosynthetic precursors, derivatives, or synthetic derivatives of such alkaloids may be therapeutically active.

It has long been known that cyclopamine, when ingested by animals, causes severe neural defects, and now its role in tumorigenesis has garnered attention. Cyclopamine can block the action of mutated genes that produce basal cell skin carcinomas, the most common form of human cancer. Studies in mouse cells suggest that cyclopamine may be used to treat a number of cancers, including medulloblastomas in the brain and rhabdomyosarcomas in muscle. Past findings also spotlight the promise of mechanism-based treatment approaches that target specific signaling pathways that are critical to a particular cancer.

Because cyclopamine and other alkaloids of the *Veratrum* superfamily may prove to be useful anti-cancer drugs, there is a need for efficient production methods for these compounds. The commercial production of alkaloids and other secondary metabolites is unpredictable in that even when a plant is known to produce a particular metabolite, it is unpredictable whether the plant cells will produce the metabolite in an undifferentiated cell culture. Ma et al. has disclosed "[a]n in vitro culture system for somatic embryogenesis and green plant regeneration of *Veratrum californicum*," but the Abstracts do not disclose production of alkaloids from undifferentiated cell culture. Ma et al., "Somatic Embryogenesis and Green Plant Regeneration from *Veratrum californicum*," 11th IAPTC&B congress Poster Sessions P-1033. Ritala et al., "Tissue culture and genetic engineering of an important anticancer compound producing plant *Veratrum californicum* Duran," Planta Medica 2006; 72. See also U.S. Pub. No. 2009/0305338. *Veratrum* alkaloids may also be produced in cultures of differentiated tissue such as shoots or roots. These differentiated tissues may be derived from initially undifferentiated tissue or through genetic transformation, e.g., hairy roots or shooty teratomas or the like. Transformed tissue may also be cultivated as suspension of undifferentiated cells. The present invention provides methods of producing alkaloids in undifferentiated cell culture.

SUMMARY OF THE PREFERRED EMBODIMENTS OF THE INVENTION

The invention provides for various methods of producing alkaloids from a plant cell culture. One objective of the invention is to obtain commercially significant amounts of the end product from large volume aerated fermentors. Another objective is to provide methods of increasing the volumetric yield.

In one embodiment, the invention provides for a method of producing one or more alkaloids from suspension cell culture by culturing plant cells of the family Liliaceae in a nutrient medium to form a cell culture that produces one or more alkaloids of the superfamily of *Veratrum* alkaloids, or a precursor of such an alkaloid or a derivative of such an alkaloid, and recovering one or more alkaloids.

In some embodiments, the plant cells are *Veratrum* or *Amianthium* cells. In a specific embodiment, the plant cells are *Veratrum californicum* cells. In preferred embodiments, the cells are undifferentiated cells, but not embryogenic cells.

In another embodiment, the plant cells are cultured in a growth medium. In a specific embodiment, the growth medium is capable of inducing a growth increase of at least 50% in one week. In another embodiment, the plant cells are cultured in a production medium.

In another embodiment, the plant cells are cultured in a growth medium and then subsequently cultured in a production medium. In a specific embodiment, the growth and the production media are different. In another specific embodiment, plant cells of the genus *Veratrum* are cultured in a growth medium that is capable of inducing a growth increase of at least 50% in one week, these plant cells are then cultured in a production medium that is different from the growth medium and that yields at least about 0.1 mg/L of one or more alkaloids of the superfamily of *Veratrum* alkaloids or precursors or derivatives thereof, and then at least one alkaloid is recovered.

In another embodiment, the invention provides for various cultures of cells such as suspension cultures of *Veratrum* cells. In a specific embodiment, the invention provides for a culture of *Veratrum* cells that is capable of producing at least about 0.1 mg/L of one or more alkaloids of the superfamily of *Veratrum* alkaloids or precursors or derivatives thereof. In another embodiment, the invention provides for a suspension culture having cells of the family of Lilliaceae and one or more alkaloids of the superfamily of *Veratrum* alkaloids in an amount of at least 0.1 mg/L. The invention also provides for alkaloids, precursors, derivatives, or extracts of these undifferentiated cell cultures.

In another embodiment, the methods and cultures described herein yield at least about 0.1 mg/L of one or more alkaloids, more preferably at least about 0.3 mg/L, at least about 0.5 mg/L, at least about 0.75 mg/L, at least about 1 mg/L, or at least about 1.5 mg/L. These yields can be measured as the production of one or more individual alkaloids or as a measure of total alkaloids.

In another embodiment, the alkaloid contains a C-nor-D-homo-[14(13→12)-abeo] ring. In preferred embodiments, the alkaloid is cyclopamine or jervine.

In another embodiment, the invention provides a method for producing one or more C-nor-D-homo-[14(13→12)-abeo] ring system-containing alkaloid compounds where undifferentiated plant cells of a plant belonging to the family Liliacaeae, and which produce one or more C-nor-D-homo-[14(13→12)-abeo] ring system-containing alkaloid compounds, are cultured in nutrient medium, and the C-nor-D-homo-[14(13→12)-abeo] ring system-containing alkaloid compounds are recovered from the resulting culture. In other embodiments, cells are cultured in the presence of biotic and/or abiotic factor(s) which stimulate and/or promote the biosynthesis of, for example, C-nor-D-homo-[14(13→12)-abeo] ring system containing alkaloid compounds.

In another embodiment, the invention provides for a method of producing a C-nor-D-homo-[14(13→12)-abeo] ring containing alkaloid compound by culturing cells of a plant belonging to the Liliaceae family, which produce a C-nor-D-homo-[14(13→12)-abeo] ring containing alkaloid compound, in a vessel in the presence of one or more stimulants which promote the biosynthesis of the C-nor-D-homo-[14(13→12)-abeo] ring containing alkaloid, and where the gas phase in the culture vessel is controlled to less than the oxygen concentration in the atmosphere from the initial stage of the culture, or wherein the dissolved oxygen concentration in a fluid medium which is in contact with the cells is controlled to less than the saturated dissolved oxygen concentration at the temperature from the initial stage of the culture, and recovering C-nor-D-homo-[14(13→12)-abeo] ring containing alkaloid compound from the resulting cultures. In another embodiment, the cells of the plant which produce the C-nor-D-homo-[14(13→12)-abeo] ring containing alkaloid compound are cultured by introducing oxygenic gas containing 0.03%-10% of carbon dioxide into the culture vessel.

BRIEF DESCRIPTION OF THE FIGURES

FIGS. 1A, B, and C show the detection of cyclopamine in a *Veratrum californicum* callus by LC-MS. FIG. 1A shows extracted single ion (m/z 412 $M^+$+H of cyclopamine). FIG. 1C shows TIC spectrum of callus extract.

FIGS. 2A, B, and C show the detection of cyclopamine in a *Veratrum californicum* callus by LC-MS. FIG. 2A shows extracted single ion (m/z 412 $M^+$+H of cyclopamine). FIG. 2C shows TIC spectrum of callus extract.

DETAILED DESCRIPTION OF THE INVENTION

Alkaloids and Alkaloid-Producing Cells

Figure 1B:
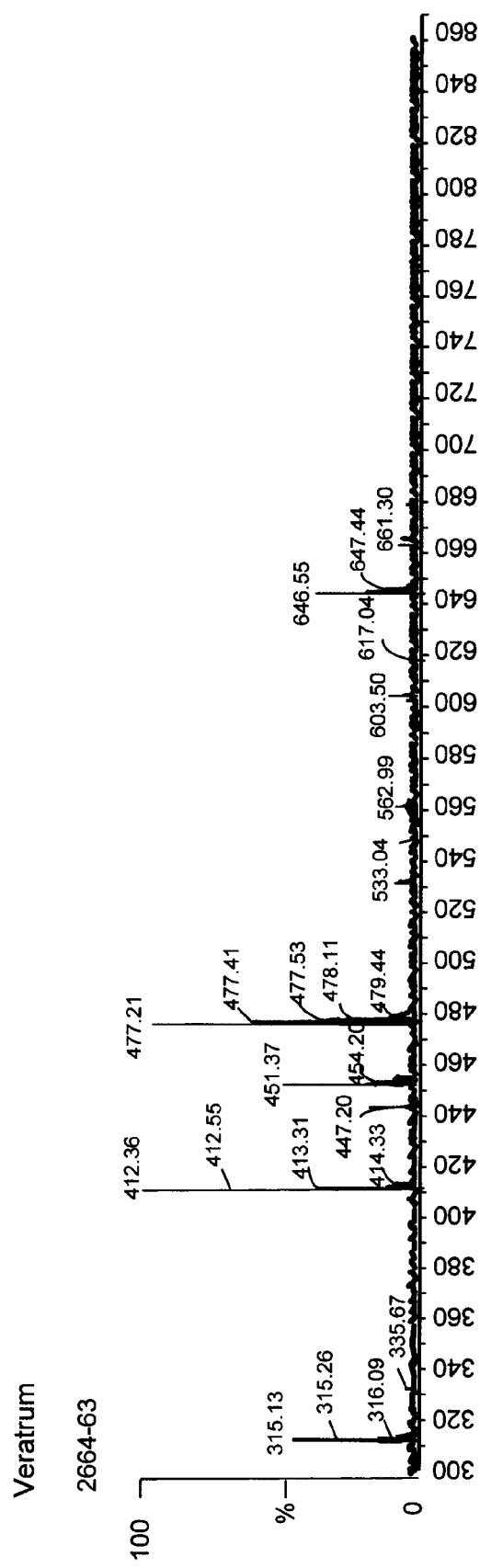
FIG. 1B shows MS spectrum of TIC peak at 3.40.

The term "alkaloid" as used herein means any member of the superfamily of *Veratrum* alkaloids as well as precursors of such an alkaloid and derivatives of such an alkaloid. In a preferred embodiment, the present invention relates to the production of a member of the superfamily of *Veratrum* alkaloids. In a preferred embodiment, the present invention relates to the production of C-nor-D-homo-[14(13→12)-abeo] ring system containing alkaloid compounds. Examples of *Veratrum* alkaloids include, but are not limited to, those listed in the table below:

TABLE 1

Exemplary *Veratrum* Alkaloids

| Name | CAS Reg. No. |
|---|---|
| Cevine | 124-98-1 |
| Geralbine | |
| Germine | 508-65-6 |
| Germine; $O^3$-(R)-2-Methylbutanoyl | 465-78-1 |
| Germine; $O^{15}$-(R)-2-Methylbutanoyl | 42138-61-4 |
| Germine; $O^{15}$-(R)-2-Methylbutanoyl, $O^3$—Ac | 465-77-0 |
| Germine; $O^{15}$-(R)-2-Methylbutanoyl, $O^3$, $O^7$-di-Ac | 508-66-7 |
| Germine; $O^{16}$-(2-Methylbutanoyl) | 135636-53-2 |
| Germine; $O^3,O^{15}$-Bis(2-methylbutanoyl) | 175030-77-0 |
| Germine; $O^3,O^{15}$-Bis(2-methylbutanoyl), $O^7$—Ac | |
| Germine; $O^{15}$-Angeloyl | 240802-94-2 |
| Germine; $O^3$-Angeloyl, $O^{15}$-(R)-2-methylbutanoyl, $O^7$—Ac | 639-11-2 |
| Germine; O-Angeloyl, O-tigloyl, O—Ac | |
| Germine; $O^3,O^{15}$-Diangeloyl, 7-Ac | 122332-72-3 |
| Germine; $O^3,O^{15}$-Bis(2-methyl-2-butenoyl) | 90541-57-4 |
| Germine; $O^3$-(2-Hydroxy-2-methylbutanoyl), $O^{15}$-(2-methylbutanoyl) | 134357-41-8 |
| Germine; $O^3$-(R)-2-Hydroxy-2-methylbutanoyl, ($O^{15}$-(R)-2-methylbutanoyl | 508-67-8 |
| Germine; $O^3$-(R)-2-Hydroxy-2-methylbutanoyl, $O^{15}$-(R)-2-methylbutanoyl, $O^7$—Ac | 560-48-5 |
| Germine; $O^3$-(2R,3R)-2,3-Dihydroxy-2-methylbutanoyl, $O^{15}$-(R)-2-methylbutanoyl | 426-34-6 |
| Germine; $O^3$-(2R,3R)-2,3-Dihydroxy-2-methylbutanoyl, $O^{15}$-(R)-2-methylbutanoyl, $O^7$—Ac | 58162-51-9 |
| Germine; $O^3$-(2S,3R)-2,3-Dihydroxy-2-methylbutanoyl, $O^{15}$-(R)-2-methylbutanoyl | 595-64-2 |
| Germine; $O^3$-(2S,3R)-(3-Acetoxy-2-hydroxy-2-methylbutanoyl), $O^{15}$-(R)-2-methylbutanoyl | 23211-84-9 |
| Germine; $O^3$-(2S,3R)-(3-Acetoxy-2-hydroxy-2-methylbutanoyl), $O^{15}$-(R)-2-methylbutanoyl, $O^7$—Ac | 465-75-8 |
| Germine; $O^{15}$-(3,4-Dimethoxybenzoyl) | 33352-59-9 |
| Germine; $O^{15}$-(3,4-Dimethoxybenzoyl), $O^3$—Ac | 33352-58-8 |
| Germine; $O^3$-(3,4-Dimethoxybenzoyl), $O^{15}$-(2-methylbutanoyl) | 142735-72-6 |
| Germine; $O^3$-(3,4-Dimethoxybenzoyl), $O^{15}$-(2-methylbutanoyl), $O^7$—Ac | 214046-03-4 |
| Germine; 1α-Acetoxy, $O^3$-(2ξ-hydroxy-2-methylbutanoyl), $O^{15}$-(2-methylbutanoyl) | 182693-36-3 |
| Hakurirodine | 56857-49-9 |
| Hakurirodine; 22R, 28-Dihydro | 38636-84-9 |
| Hakurirodine; 22R, 28-Dihydro, 3-O—Ac | 38636-85-0 |
| Hosukinidine | 72765-23-2 |
| Isorubijervine | 468-45-1 |
| Isorubijervine; $O^3$-β-$_D$-Glucopyranoside | 468-46-2 |
| Isorubijervine; 12β-Hydroxy | 164178-46-5 |
| Jervine | 469-59-0 |
| Jervine; O—Ac (O-Acetyljervine) | 14788-78-4 |
| Jervine; N-Methoxycarbonyl (Verapatuline) | |
| Jervine; N-(2-Methoxycarbonylethyl) (Methyl jervine-N-3'-propanoate) | 132943-48-7 |
| Jervine; $O^3$-β-$_D$-glucopyranoside (Pseudojervine) | 36069-05-3 |
| Jervine; 3-Ketone (Jervinone) | |

TABLE 1-continued

Exemplary *Veratrum* Alkaloids

| Name | CAS Reg. No. |
|---|---|
| Jervine; 11β-Alcohol (Veratrobasine) | 20226-97-5 |
| Jervine; 11β-Alcohol, 3,11-di-Ac | |
| Jervine, 11-Deoxo (Cyclopamine) | 4449-51-8 |
| Jervine, 11-Deoxo, O,N-di-Ac | |
| Jervine; 11-Deoxo, 3-O-β-$_D$-glucopyranoside (Cycloposine) | 23185-94-6 |
| Jervine; 1α-Hydroxy, 5α,6-dihydro | |
| Loveraine | |
| 20-(2-Methyl-1-pyrrolin-5-yl)pregn-4-en-3-one | 55486-07-2 |
| Neoverataline A | |
| Neoverataline A; 7α-Hydroxy | |
| Petisidinine; 3-Ac | |
| Procevine | 468-24-6 |
| Protoverine; $O^6,O^7$-Di-Ac, $O^{15}$-(R)-2-methylbutanoyl, $O^3$-(+)-2-hydroxy-2-methylbutanoyl | 143-57-7 |
| Protoverine; $O^6,O^7$-Di-Ac, $O^{15}$-(R)-2-methylbutanoyl, $O^3$-(+)-threo-2,3-dihydroxy-2-methylbutanoyl | 124-97-0 |
| Protoverine; $O^6$—Ac, $O^{15}$-(R)-2-methylbutanoyl, $O^3$-(+)-2-hydroxy-2-methylbutanoyl | 67375-42-2 |
| Protoverine; $O^6$—Ac, $O^{15}$-(R)-2-methylbutanoyl, $O^3$-(+)-threo-2,3-dihydroxy-2-methylbutanoyl | 67370-03-0 |
| Protoverine; $O^6,O^7$-Di-Ac, $O^{15}$-(R)-2-methylbutanoyl, $O^3$-angeloyl | 663-93-4 |
| Protoverine; 3-[(2S,3R)-2,3-Dihydroxy-2-methylbutanoyl], $O^6,O^7$-di-Ac, $O^{15}$-(R)-2-methylbutanoyl | 82535-71-5 |
| Protoverine; $O^3$-(2-Hydroxy-2-methylbutanoyl), $O^{15}$-(2-methylbutanoyl) | |
| Rubijervine | 79-58-3 |
| Rubijervine; 12-Epimer | 472-00-4 |
| Rubiverine | |
| 16,28-Secosolanida-5,22(28)-diene-3,16-diol, $_{9CI}$; (3β,16α,20S,25α)-form | 29271-49-6 |
| 16,28-Secosolanida-5,22(28)-diene-3,16-diol, $_{9CI}$; (3β,16α,20S,25α)-form, 3-O-β-$_D$-Glucopyranoside | 54557-67-4 |
| 16,28-Secosolanida-5,22(28)-diene-3,16-diol, $_{9CI}$; (3β,16α,20S,25α)-form, 16-Ac | 36506-65-7 |
| 16,28-Secosolanida-5,22(28)-diene-3,16-diol, $_{9CI}$; (3β,16α,20S,25α)-form, 16-Ac, 3-O-β-$_D$-glucopyranoside | 30511-97-8 |
| 16,28-Secosolanid-5-ene-3,16-diol; (3β,16α,22R,25S)-form | 65027-01-2 |
| 16,28-Secosolanid-5-ene-3,16-diol; (3β,16α,22S,25S)-form | 65027-00-1 |
| 16,28-Secosolanid-5-ene-3,16-diol; (3β,16α,22S,25S)-form, 16-Ac | 36069-45-1 |
| Shinonomenine | 70598-84-4 |
| Solanidine, O-β-$_D$-Galactopyranoside | 511-37-5 |
| Synaine | |
| Tienmulilmine | |
| Tienmulilminine | |
| Veracevine; 3-(Z)-2-Methyl-2-butenoyl | 62-59-9 |
| Veracintine | 33596-06-4 |
| Veracintine; 3-O-β-$_D$-Glucopyranoside | 67006-43-3 |
| Veracintine; 3-O-α-$_L$-Rhamnoside | 110934-18-4 |
| Veraflorizine | 70598-85-5 |
| Veragenine | |
| Veralbidine | |
| Veralinine | |
| Veralinine; Stereoisomer, 3-β-$_D$-Glucopyranoside | 58078-63-0 |
| Veralkamine | 17155-31-6 |
| Veralkamine; O,O-Di-Ac | 195244-85-0 |
| Veralkamine; 5α,6,12,13-Tetrahydro | 17155-36-1 |
| Veralobine | 6242-49-5 |
| Veralodine | 41787-59-1 |
| Veralodisine | 52617-23-9 |
| Veralodisine; 3-O-β-$_D$-Glucopyranoside | 56598-27-7 |
| Veralosidinine | 52389-14-7 |
| Veramanine | 182816-87-1 |
| Veramarine | 4565-85-9 |
| Veramine | 21059-48-3 |
| Veraminine | |
| Veramitaline | 313697-00-6 |
| Veranovine | |
| Verareine | |
| Veratramine | 60-70-8 |
| Veratramine; $O^3$-β-$_D$-Glucopyranoside | 475-00-3 |
| Veratramine; 23-Deoxy | |
| Veratramine; 20-Epimer | |
| Veratramine; 20-Epimer, $O^{23}$-β-$_D$-glucopyranoside | 148440-62-4 |
| Veratra-5,11,13-triene-3,23-diol; (3β,22S,23R,25S)-form, 23-O-β-$_D$-Glucopyranoside | 148440-63-5 |
| Veratrenone | 55839-66-2 |
| Verazine | 14320-81-1 |
| Verazine; 22S,N-Dihydro | 17463-47-7 |
| Verazine; 22S,N-Dihydro, 3-O-β-$_D$-glucopyranoside | 128351-76-8 |
| Verazine; 12β-Hydroxy, 22S,N-dihydro | 164178-47-6 |
| Verazine; 20-Epimer | 145033-50-7 |
| Verdine | 73667-53-5 |
| Verine | |
| Vertaline B | 118985-28-7 |
| Vertaline B; 16-Deoxy | 91423-75-9 |
| Vertaline B; 16-Deoxy, 3-O-β-$_D$-glucopyranoside | 128351-77-9 |
| Zygadenilic acid δ-lactone | |
| Zygadenilic acid δ-lactone; $O^{16}$-Angeloyl | |
| Zygadenine; $O^3$—Ac | 2777-79-9 |
| Zygadenine; $O^3$-(R)-2-Methylbutanoyl | |
| Zygadenine; $O^3$-Angeloyl | 67370-02-9 |
| Zygadenine; $O^3$-Angeloyl, β-N-oxide | 313677-61-1 |
| Zygadenine; $O^3$-(3,4-Dimethoxybenzoyl) | 31329-58-5 |

In one embodiment, the alkaloid is an alkaloid capable of being produced from a *Veratrum* or *Amianthium* cell. In another embodiment, the alkaloid is an alkaloid capable of being produced from a *Veratrum* cell. In one embodiment, the alkaloid itself possesses therapeutic activity, or it can be modified to yield bioactive compounds. In a preferred embodiment, the alkaloid contains a C-nor-D-homo-[14(13→12)-abeo] ring. In another preferred embodiment, the alkaloid is cyclopamine or jervine.

The method includes culturing alkaloid-producing cells to produce one or more alkaloids, as defined above. The term "alkaloid-producing cells" refers to any cells capable of producing one or more alkaloids under at least one set of culture conditions. In preferred embodiments, "alkaloid-producing cells" refers to cells which produce one or more alkaloids in a detectable amount under the culture conditions of the embodiment.

In the alkaloid production methods described herein, the cell culture comprises cells of the family Liliaceae. In one preferred embodiment, the cell culture comprises cells of the genera *Veratrum* and/or *Amianthium*. In a more preferred embodiment, the cell culture comprises *V. californicum* cells. The cells in culture can be the same as or different from one another. For example, the cells can be from one or more genera, species, variants, or strains. The cells can be naturally-occurring, or they can be hybrids or genetically altered cells. Exemplary plant cells include, but are not limited to, those listed in the table below:

TABLE 2

Exemplary cell species useful for alkaloid production

| Exemplary Genus | Exemplary Species | Exemplary Sub-Species/ Varieties |
|---|---|---|
| *Amianthium* | muscitoxicum | |
| *Fritillaria* | camtschatcensis | |
| *Schoenocaulon* | officinale | |

TABLE 2-continued

Exemplary cell species useful for alkaloid production

| Exemplary Genus | Exemplary Species | Exemplary Sub-Species/Varieties |
|---|---|---|
| Veratrum | album | ssp. *album*, ssp. *oxysepalum*, ssp./var. *lobelianum*, var. *Grandiflorum* |
| Veratrum | calfornicum | var. *calfornicum*, var. *Caudatum* |
| Veratrum | eschholtzii | |
| Veratrum | fimbriatum | |
| Veratrum | grandiflorum | |
| Veratrum | lobelianum | |
| Veratrum | maackii | |
| Veratrum | nigrum | var. *Ussuriense* |
| Veratrum | oblongum | |
| Veratrum | officinalis | |
| Veratrum | oxysepalum | |
| Veratrum | patulum | |
| Veratrum | sabadilla | |
| Veratrum | stamineum | |
| Veratrum | stenophyllum | |
| Veratrum | taliense | |
| Veratrum | viride (viridae) | var. Verabore |
| Veratrum | woodii | |
| Zygadenus | gramineus | |
| Zygadenus | paniculatus | |
| Zygadenus | venenosus | |

The tissue used to initiate cell culture can be selected based on, for example, ability to favor the production of one or more particular alkaloids.

The cell culture can be a callus culture. A callus is a substantially undifferentiated cell mass cultured on solidified medium. Methods for callus formation and callus propagation are generally known in the art. In one embodiment, a callus is initiated by any viable part of the monocotyledonous plant, preferably immature embryos of the monocotyledonous plant. For example, cell culture initiation can include surface sterilizing plant source material, e.g., by washing thoroughly with clean water, using a disinfectant such as hypochlorite, using wetting agents such as Tween or Triton, using antibiotics, and/or using antifungal agents. The plant part can be used intact, or a portion of it can be used, such as an embryo removed from a seed. Typically, the plant part is placed on the surface of solidified medium and incubated in a sterile environment for about 1-12 weeks, until a mass of undifferentiated cells (the callus) grows in proximity to the plant part. After establishing the callus culture, the cells are cultured in a nutrient medium as described in further detail below. The undifferentiated cells can be distinguished from embryogenic cells by the presence of a vacuole because embryogenic cells are highly cytoplasmic and non-vacuolated.

For callus propagation, culture conditions including media components, pH ranges, carbon sources, nitrogen sources, macro-salts and micro-salts, vitamins, and growth regulators are all described, for instance, in Bringi WO 97/44476, incorporated in its entirety herein by reference. In one embodiment, callus propagation comprises using a gelling agent, anti-browning agent, charcoal, and/or light/dark cycles. Gelling agents include, for example, agar, hydrogels, gelatin, and gelrite. Charcoal can be used for removing wastes and undesirable organic compounds. An exemplary inoculum is about 0.01 to about 10 g/25 ml. Subculturing techniques known in the art can be used for periodic serial transfer of portions of callus into a fresh source of nutrients.

The cell culture for producing alkaloids can be a suspension culture. The term "suspension culture" is used to describe structurally undifferentiated cells that are dispersed in a liquid nutrient medium. It is understood that suspension cultures comprise cells in various stages of aggregation. A range of aggregate sizes are encountered in the suspensions with sizes ranging from tens of microns in diameter (single cells or few-aggregated cells) to aggregates many millimeters in diameter, consisting of many thousands of cells. Generally, suspension culture can be initiated using a culture medium that was successful in callus culture, without gelling agents, although optimized media for suspension culture may differ from the optimum for callus of the same cell line. A cell culture may also be optionally derived from a cryopreserved collection of cells.

Cryopreservation Via 2-Step Method

In one embodiment, the invention provides a 2-step method for the induction of desication tolerance in *Veratrum* plant cell suspension cultures, as well as dehydration and cryoprotection steps prior to freezing of the plant cell suspension cultures in cryogenic conditions. Cell suspensions of *Veratrum* plant cells typically contain many large cell aggregates, and alternative cryopreservation methods such as for example vitrification are disadvantageous for use with *Veratrum* plant cell suspensions when the plant cell suspension cultures contain a significant amount of highly aggregated plant cells, unless steps are taken to minimize cell aggregation. Vitrification solutions have a very high osmolarity, which can cause the cells on the outside of the aggregate to become injured by the vitrification solution before the vitrification solution penetrates the cells located in the internal portions of the cell aggregate. This phenomenon makes the timing of exposure to vitrification solutions very difficult to determine, and thus undesirable for use with plant cells that are substantial aggregates. However, in one embodiment of the invention discussed below, cell aggregates are substantially eliminated thereby allowing the use of vitrification methods.

Accordingly, the methods of the invention were developed as an effective means of cryopreserving *Veratrum* plant cell suspensions with a high level of restoration of cellular function following thawing of the cryopreserved plant cells. In one embodiment of the invention, the method provides greater than 50% recovery of viable cells following thawing of the cryopreserved *Veratrum* plant cells using the cryopreservation techniques set forth herein. In another embodiment of the invention, the method provides greater than 75% recovery of viable cells following thawing of the cryopreserved *Veratrum* plant cells using the cryopreservation techniques set forth herein.

When cryopreservation is desired, *Veratrum* plant cell suspension cultures that are to be cryopreserved are pre-cultured in liquid GM (IND64) media for about 7 to about 10 days. In a preferred embodiment of the invention, the plant cell suspension culture is a plant cell suspension culture comprising undifferentiated cells. Cell suspensions should be transferred to fresh media every about 7 to about 10 days. Subsequently, the plant cell suspension cultures are transferred to solidified GM (IND64) media comprising about 0.8% agarose to about 1% agarose and cultured in the dark for about 7 days to about 10 days at 25° C.

TABLE 3

| GM (IND64) Media* | |
|---|---|
| Component | Amount |
| Sucrose | 20 g/L |
| SH Macro (10X) | 100 ml/L |

TABLE 3-continued GM (IND64) Media*

| Component | Amount |
|---|---|
| SH Micro (1000X) | 1 ml/L |
| Iron Stock (50X) | 10 ml/L |
| SH Vitamins (50X) | 20 ml/L |
| Dicamba (10 mM) | 1 ml/L |

*About 8 g/L or more of agarose is added to the formulation to make solid media. Final pH of about 5.6.

In this embodiment following pre-culturing of the *Veratrum* plant cells on solid GM (IND64) media for a period of between about 7 to about 10 days, the plant cells are cryopreserved using the 2-step cryopreservation methods of the invention. Cryopreservation methods of the invention involve transferring the *Veratrum* plant cells into liquid GM media comprising from about 0.3M to about 0.5M sorbitol or sucrose, and culturing the *Veratrum* plant cells for about 16 hours to about 48 hours on a rotary shaker (120 rpm). In a preferred embodiment of the invention, the transferred *Veratrum* suspension plant cells are small aggregates of plant cells.

In another embodiment of the invention, the transferred *Veratrum* plant cells are substantially small-aggregated through the use of, e.g., a Bellco homogenizer and a Bellco Cellector™ Tissue Sieve (10 mesh/1910 μm and 20 mesh/860 μm) (Bellco Biotechnology, Vineland, N.J.).

The liquid GM media is removed and the *Veratrum* plant cells are subsequently transferred into liquid Cryopreservation 1 media. Table 4 provides the components of the Cryopreservation 1 media.

TABLE 4

Cryopreservation 1 Media
Components

Liquid GM media [IND64]
Selected Sugar* [0.5M-1.0M]
DMSO [5.0-10.0%]

*By a selected sugar is intended a neutral sugar, an alcohol sugar, sucrose, maltose, trehalose or glycerol. Neutral sugars include but are not limited to glucose, arabinose, xylose, mannose, galactose, rhamnose or glucuronic acid. Alcohol sugars include but are not limited to maltitol, sorbitol, xylitol, isomalt, lactitol, erythritol or mannitol.

Figure 5A:
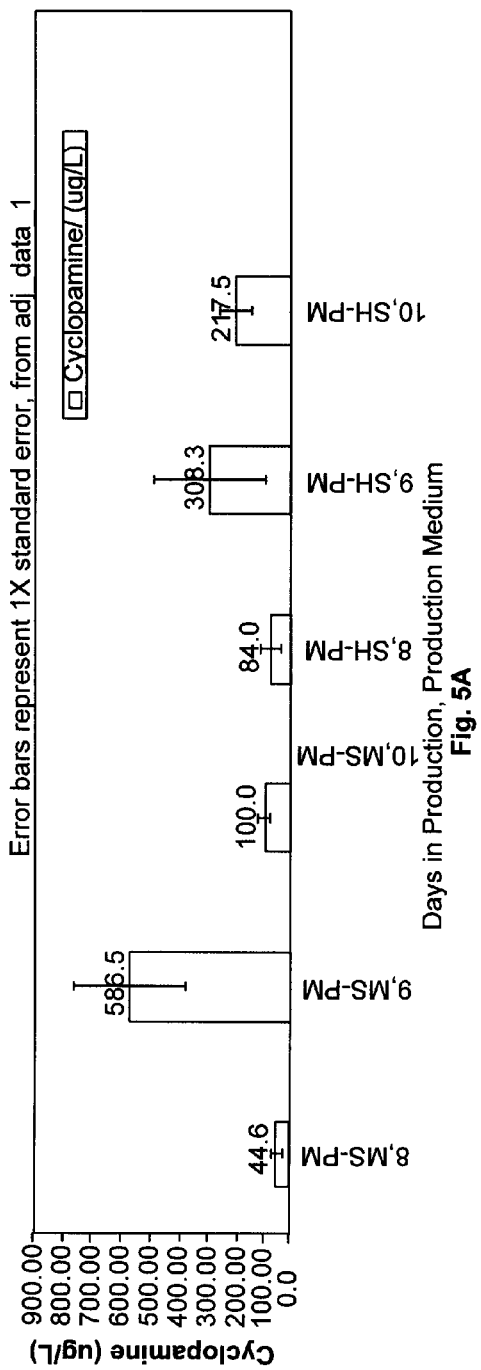
FIGS. 5A and B show cyclopamine titers in MS- and SH-based production medium on days 8, 9, and 10 using a *Veratrum californicum* suspension culture. Fig. B shows the data not including outliers from dry wells.
Figure 5B:
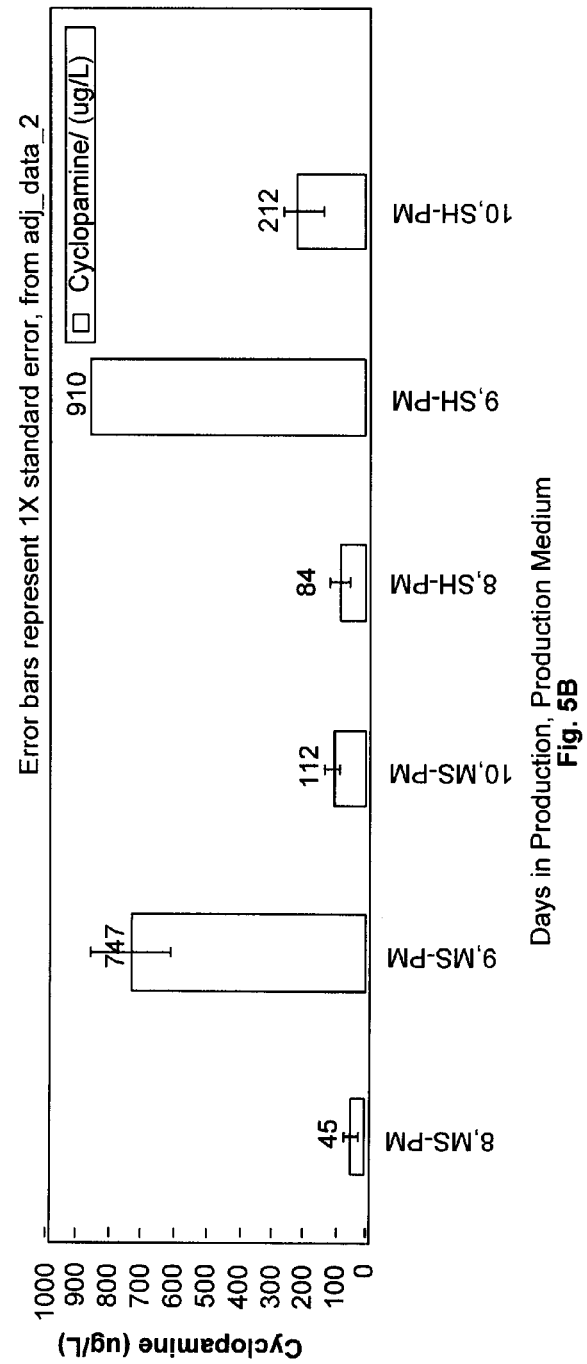
Figure 6:
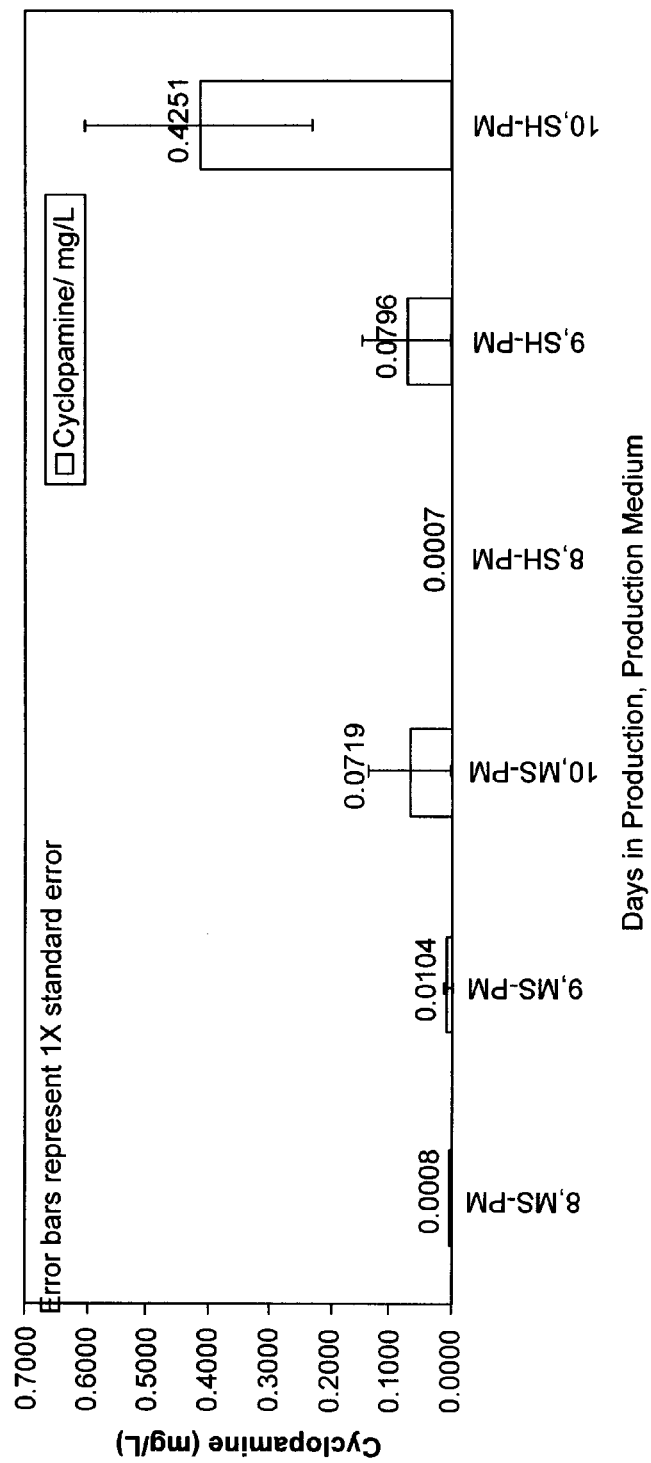
FIG. 6 shows cyclopamine titers in MS- and SH-based production medium on days 8, 9, and 10 using a *Veratrum californicum* suspension culture.
Figure 7:
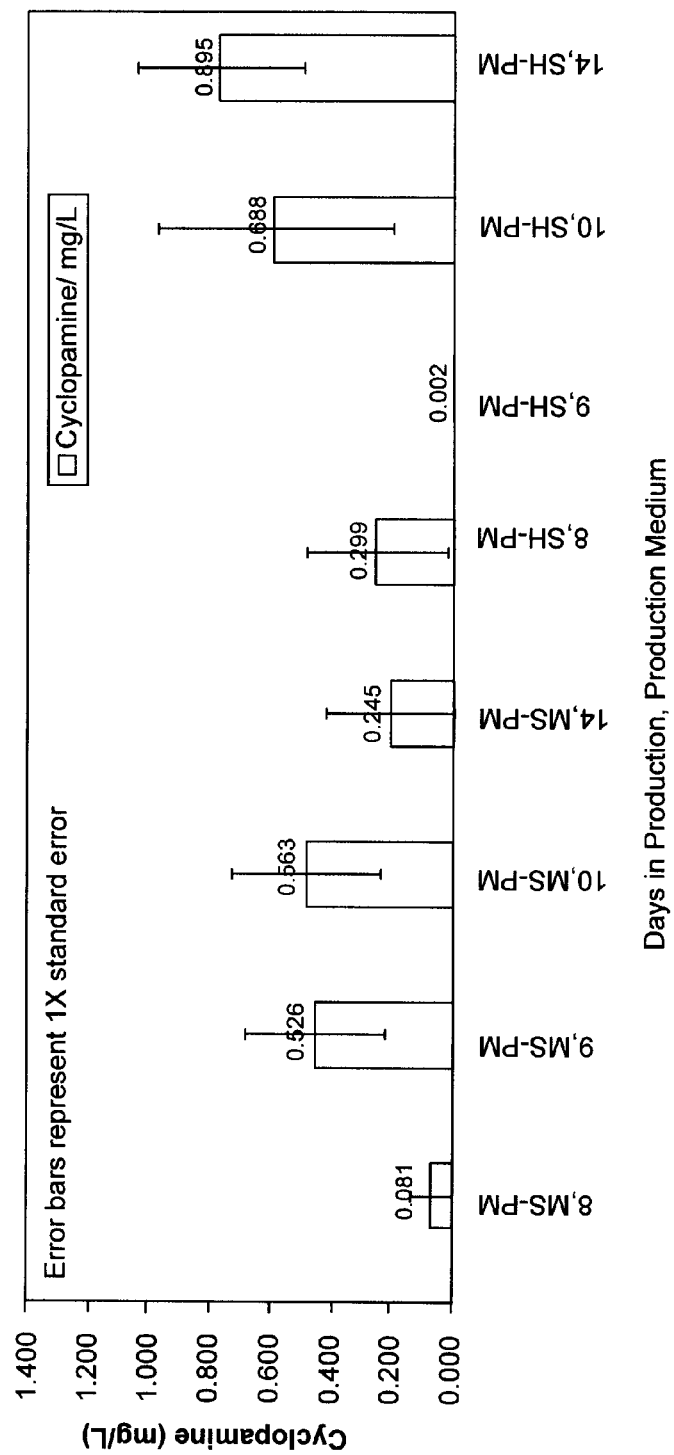
FIG. 7 shows cyclopamine titers in MS- and SH-based production medium on days 8, 9, and 10 using a *Veratrum californicum* suspension culture.

In a preferred embodiment of the invention, the Cryopreservation 1 media comprises about 6% DMSO. The *Veratrum* plant cells are incubated in the Cryopreservation 1 media for no less than about 2 hours to no greater than about 4 hours on ice, after which time 2 ml volumes of the plant cell suspension are transferred in Cryopreservation 1 media to cryo-vials. The transferred plant cell suspension cryo-vials are then cooled to from 0° C. to −40° C. at a rate of −0.33 to −1° C. per minute. Following cooling, the cryo-vials are submerged in liquid nitrogen and stored in a liquid nitrogen tank. FIGS. 5-7 demonstrate recovery of cryopreserved *Veratrum* plant cell culture that may be obtained by performing a cryopreservation technique consistent with the teachings provided herein.

Cryopreservation Via Vitrification

In another embodiment of the invention, following pre-culturing of the *Veratrum* plant cells on solid GM (IND64) media for a period of between about 7 to about 10 days the plant cells are cryopreserved using vitrification techniques. In this embodiment of the invention, *Veratrum* plant cells are transferred into liquid GM (IND64) media comprising about 0.3M to about 0.5M sorbitol or sucrose, and the plant cells are cultured for about 16 hours to about 48 hours on a rotary shaker (120 rpm). In a particularly preferred embodiment of the invention, the transferred *Veratrum* suspension plant cells are small-aggregated plant cells produced using a Bellco homogenizer and a Bellco Cellector™ Tissue Sieve (20 mesh/860 um) (Bellco Biotechnology, Vineland, N.J.).

Next, the liquid GM (IND64) media is removed and 10-30% w/v of fresh *Veratrum* plant cells are subsequently transferred into Cryopreservation 2 media. The composition of Cryopreservation 2 media is provided in Table 5. If necessary, the pH is adjusted to between about pH 5-7.

TABLE 5

Cryopreservation 2 Media
Components

Selected Sugar* [0.2M-0.5M]
Permeating Agent [DMSO 0-25% and/or Ethylene Glycol 0-2M]
Selected Trisaccharide** [50-200 mM]

*By a selected sugar is intended a neutral sugar, an alcohol sugar, sucrose, maltose, trehalose or glycerol. Neutral sugars include but are not limited to glucose, arabinose, xylose, mannose, galactose, rhamnose or glucuronic acid. Alcohol sugars include but are not limited to malitiol, sorbitol, xylitol, isomalt, lactitol, erythritol or mannitol.
**By a selected trisaccharide is intended melezitose, panose, raffinose, kestose or lactosucrose.

Preferably, the *Veratrum* plant cells are incubated in the Cryopreservation 2 media (cell density=20%) for about 2 hours to about 4 hours at about 4° C., after which time the Cryopreservation 2 media is removed. About one part of the Cryopreservation 2 media-treated *Veratrum* plant cells are weighed and added into each cryo-vial. About 5 parts by weight of Cold Cryoprotectant Solution is added into each cryo-vial and the cells are chilled at 0° C. (on ice) prior to submersion in liquid $N_2$. The composition of Cold Cryoprotectant Solution is provided in Table 6. Immediately following this incubation, the cryo-vial is submerged in liquid nitrogen.

TABLE 6

Cold Cryoprotectant Solution Media
Components

Selected Sugar* [1.0-2.0M]
Divalent Cation [5.0-10.0 mM]
Permeating Agent [DMSO 0-50% or Ethylene Glycol 0-10M]

*By a selected sugar is intended a neutral sugar, an alcohol sugar, sucrose, maltose, trehalose or glycerol. Neutral sugars include but are not limited to glucose, arabinose, xylose, mannose, galactose, rhamnose or glucuronic acid. Alcohol sugars include but are not limited to malitiol, sorbitol, xylitol, isomalt, lactitol, erythritol or mannitol.

Thawing and Recovery

The present invention also provides methods for the thawing and recovery of cryopreserved *Veratrum* plant cell suspensions. In one embodiment of the invention, cryovials comprising cryopreserved *Veratrum* plant cell suspensions are thawed at a temperature range of about 37° C. to about 42° C., in a water bath or other sustained temperature environment, with occasional agitation or gentle stirring for 3 to 5 minutes or until the frozen cells have thawed.

Following thawing and sterilization of the cryovials (typically by ethanol exposure), if the 2-step method is used, the contents of the cryovials are passed through a suction filter to remove the cryopreservation solution, and the cells on the filter paper are transferred to solid GM (IND64) media, and incubated at 25° C. in the dark for 16-24 hours. Thawed cells are transferred to fresh media about every 7 days until 1-2 grams of biomass are produced. If the vitrification method is used, the contents of each thawed and sterilized cryo-vial is poured/diluted in 10 mls of media containing about 5-10 mM divalent cations and about 0.1-1.0 M of a selected sugar for 10 minutes, then passed through a suction filter to remove the solution, and the cells on the filter paper are transferred to solid GM (IND64) media and incubated at 25° C. in the dark for about 16 to about 24 hours. Then, the filter paper with cells is transferred to fresh solid GM (IND64) medium and then transferred every 7 days to fresh GM medium at 25° C. in the dark for restoration of cell functions.

Cell Culture: Nutrient Medium

The methods of the present invention include a step of culturing the cells in a nutrient medium. The method can also include more than one step of culturing the cells in a nutrient medium. The term "nutrient medium" means a medium that is suitable for the cultivation of plant cell callus and/or suspension cultures. The term "nutrient medium" is general and encompasses both "growth medium" and "production medium." A "growth medium" is a nutrient medium that favors growth of cultured cells. In preferred embodiments, the growth medium provides a growth increase of at least 50% in one week. A "production medium" is a nutrient medium that favors the production of one or more alkaloids. While growth can occur in a production medium, production can take place in a growth medium, and both growth and production can take place in a single nutrient medium, a production medium favors the production of target compounds relative to the growth medium. The method described herein can include one or more steps of culturing the cells in a growth medium and/or one or more steps of culturing the cells in a production medium.

In the context of non-growth-associated secondary metabolites, a production medium preferably has a) an increased level of sucrose or other carbon course, and/or b) a reduced level of an inorganic component such as nitrate, ammonium, phosphate, and/or potassium, and/or c) a different calcium level as compared to the growth medium. See U.S. Pat. No. 4,717,664. One of ordinary skill in the art recognizes that cell growth is generally favored by a balanced or relatively low ratio of carbon to inorganic components such as nitrogen and phosphate, while cell growth is limited by a relatively high ratio of carbon to inorganic components. Accordingly, the production medium may utilize growth limiting conditions, e.g., a high ratio of carbon to inorganic components, to promote alkaloid production as opposed to cell growth. See, e.g., Sakuta M. & Komamine A., "Cell Growth and accumulation of Secondary Metabolites", Cell culture and Somatic Cell Genetics of Plants, Chapter 5, Vol. 4, pp. 97-114 (1987); Majerus F. & Pareilleux A., "Alkaloid accumulation in Ca-alginate entrapped cells of *Cutharanthus roseus*: Using a limiting growth medium", Plant Cell Reports (1986) 5: 302-305. Nutrient media can be based on Murashige and Skoog Basal Salts (MS) or Schenk and Hildebrandt Basal Salts (SH) (Sigma-Aldrich). Exemplary production media (PM) include, but are not limited to, media containing a salt base (e.g., MS or SH), plus macronutrients, micronutrients, vitamins, 5% sucrose, 100 µM methyl jasmonate (MJS), and 20 µM Dicamba. Exemplary growth media include, but are not limited to, media containing a salt base (e.g., MS or SH), plus 2% sucrose, and 10 µM Dicamba.

In one embodiment, the cells are first cultured in a growth medium, and then the cells are cultured in a production medium that is different from the growth medium. When cells are transferred from a growth medium to a production medium, the production medium preferably has a higher level of carbon source and/or C:N ratio, e.g., a higher concentration of a saccharide. The production medium also preferably comprises sources of inorganic or organic nitrogen such as an amino acid. Other components of the nutrient medium can be introduced into the culture after the cells and medium are first contacted. In one embodiment, these ingredients, such as additional saccharide, are supplied in a feed stream intermittently or continuously as needed. Of course since the alkaloid products contain nitrogen, it is desirable to provide adequate nitrogen to sustain and improve the accumulation of the desired products.

The desired effect, e.g., growth or production, can be achieved by manipulating other reaction conditions including, but not limited to, temperature, pH, and light/darkness; by manipulating the media conditions by adding, removing, or changing the concentration of one or more nutrients or other agents; or by manipulating any combination of these conditions. In some preferred embodiments, the desired effect is achieved by manipulating the medium. In particular, suspension cultures producing alkaloids are capable of rapid growth rates and high cell densities when suitable nutrients and reaction conditions are used. One of ordinary skill in the art can readily incorporate, modify, and manipulate media conditions in view of the guidance provided herein to achieve optimum performance, which may be expected to vary between cell lines.

The alkaloids of the present invention are secondary metabolites that are produced through a series of many enzymatic steps, requiring coordinated action of many different enzymes to produce and sequentially modify precursors that are ultimately converted into target secondary metabolites. At the same time, secondary metabolite production will be lowered if other enzymes metabolize precursors of the desired metabolite, draining the precursor pools needed to build the secondary metabolites. Stimulators of particular enzymes or inhibitors of other enzymes may therefore enhance the rate and/or final yield of secondary metabolites in culture of particular cell lines. In addition to nutrients typically employed in plant cell culture, other ingredients can be included to improve alkaloid production. In one embodiment, the nutrient medium includes at least one component selected from enhancement agents, elicitors, stimulants, precursors, inhibitors, growth regulators, heavy metals, and ethylene inhibitory compounds.

Adding one or more enhancement agents to the cell culture may improve alkaloid production. Enhancement agents include, but are not limited to, anti-senescence agents, agents affecting either the biosynthesis or action of ethylene, plant growth regulators, precursors, inhibitors of competing reactions for precursors or the desired products, elicitors, jasmonate and related compounds of the 12-oxo-phytodienoic acid pathway, compounds having auxin-like activity and precursors thereof, and compounds having cytokinin-like activity. Adding precursors into the culture medium including, but not limited to, cholesterol and/or acetate and/or salts thereof may improve the biosynthesis rate and/or final yield. Such precursor feeding might be combined with other factors like, but not limited to, inhibitors of undesired biosynthetic pathways and/or stimulation of the desired biosynthetic pathway e.g. by light.

The production of indole alkaloids in *Catharanthus roseus* cell cultures is known to be suppressed by added auxin-like compounds; likewise, in the culture medium for alkaloid production, omitting or lowering the content of auxin-like substances improved production. Improvement of alkaloid production by selected enhancement agent(s) can be experimentally confirmed.

The rate of alkaloid production is determined not by a single rate-limiting step, but by a complex interaction between a plurality of limiting factors. Relief of any one of the limiting factors will enhance alkaloid production, although the magnitude of the enhancement will depend on particular culture conditions, which determine the relative limiting effects of other steps in alkaloid production once a particular limitation has been relieved. Culture conditions that affect the interaction between various limiting factors include: the genetic make up of the cells; the composition of the culture medium; and the gaseous environment, temperature, illumination, and process protocol. The enhancement agent(s) added to a particular culture will usually be selected in view of the limiting factors in that culture, which may be determined empirically by comparing the effects of individual enhancement agents as set forth herein. Typical quantities of enhancement agents for cell culture are known in the art.

Elicitors include, but are not limited to, jasmonic acid, methyl jasmonate, natural or synthetic jasmonates, tuberonic acid, cucurbic acid, coronatine, indanoyl amides such as 6-ethyl-indanoyl isoleucine, alkanoic acids, 12-oxo-phytodienoic acid, systemin, volicitin, and compounds related to any of these exemplary elicitors. Elicitors also include, but are not limited to, oligosaccharides, e.g., oligosaccharides from plants, fungi, or microbes; chitosan; chitin; glucans; cyclic polysaccharides; preparations containing cellular material from bacteria, fungi, yeasts, plants, or insects; material contained in insect saliva or secretions; inhibitors of ethylene biosynthesis or action in plants, especially silver-containing compounds or complexes, cobalt, and aminoethoxyvinylglycine.

Elicitors especially useful for the production of the *Veratrum* alkaloids include jasmonic acid-related compounds such as jasmonates, cucurbates, and tuberonates. Indanoyl amides are also useful elicitors. Heavy metals such as cadmium, vanadium and silver are useful in salt or complex form. Chitin, chitosans (especially chitosan glutamate), N-acetyl oligosaccharides, pectic polysaccharides, fungal glycans (containing 5 or more sugars), fungal glycoproteogalactans, sphingolipid elicitors, pectic polysaccharides, and arachidonic acid are also useful elicitors.

Exemplary growth regulators and inhibitors include, but are not limited to, those disclosed in Bringi WO 97/44476. These can be used singly or in any combination. In general, plant growth regulators include a wide variety of substances readily known from the general plant literature. Of these, growth regulators particularly suitable for *Veratrum* cultures include, but are not limited to, auxin and/or cytokinin-like compounds, e.g., indoleacetic acid, indolebutyric acid, naphthalene acetic acid (NAA), phenoxyacetic acid and halogen substituted phenoxyacetic acids, picloram, dicamba, benzylaminopurine, kinetin, zeatin, thidiazuron, and indole acetic acid. Amino acids include any natural or synthetic amino acid utilized by the cells such as glutamine, glutamic acid, and aspartic acid.

Other compounds including, but not limited to, alpha amino isobutyric acid (which simulates rol C-induction) and/or alpha DL-di-fluormethylornithine (which can induce a similar phenotype/biochemical situation to that induced by RI-T-DNA) might be added to the culture medium in order to reduce unrelated compounds and/or in order to improve product yields.

It is also desirable to reduce or avoid oxidative browning in the cell culture. Thus, anti-browning agents may be added to inhibit the oxidation of phenolic exudates. Preferably, the cells in culture are undifferentiated cells, which are less susceptible to browning than embryonic cells.

Suggested concentration ranges for these medium components are provided below, but routine optimization may demonstrate preferred conditions outside these ranges for particular cell lines and/or particular culture conditions. All concentrations refer to average initial values in the extracellular medium after addition. Concentrations in feed solutions and therefore, locally, concentrations in contact with the cells could be higher than that indicated. Elicitors, such as jasmonic acid-related compounds, can be used at doses of about 0.01 μmol/L to about 1 mmol/L, preferably about 1 μmol/L to about 500 μmol/L. Preparations containing cellular material can be added based on the concentration of a specific constituent of the preparation or as some fraction of the culture volume. Heavy metals and ethylene inhibitors such as silver salts or complexes, can be used at concentrations up to about 1 mmol/L, preferably about 0.01 μmol/L to about 500 μmol/L. Other inhibitors of metabolic pathways can be used at concentrations of about 1 μmol/L to about 5 mmol/L. Aromatic compounds including a methylenedioxy functionality can be included at concentrations of about 0.1 μmol/L to about 5 mmol/L, preferably about 1 μmol/L to about 2 mmol/L. Growth regulators such as compounds with auxin-like activity; compounds with cytokinin-like activity; compounds with giberrelic acid-, absicic acid-, or brassinosteroid-like activity, can be used at concentrations of about 0.001 μmol/L to about 2 mmol/L, preferably about 0.01 μmol/L to about 1 mmol/L. Precursors, such as amino acids or terpenoid precursors, can be used at concentrations of about 1 μmol/L to about 20 mmol/L, preferably about 10 μmol/L to about 10 mmol/L. Using these suggested concentrations as a guide, routine optimization can discern which component, or combination of components, and which concentrations, including concentrations beyond the suggestions above, are useful to maximize alkaloid production.

Cell Culture: Other Reaction Conditions

As described above, the cells can be cultured under conditions to favor production and/or growth. In addition to modifying the medium components, other reactions conditions can also be modified to obtain the desired result. For instance, the temperature range can be adjusted. Preferred temperatures include about 0° C. to about 35° C., more preferably about 15° C. to about 35° C., and even more preferably about 20° C. to about 30° C. Likewise, one can alter the periods of the light/dark cycle, or one can apply within a production cycle a first period of time more than 24 hours—in the dark followed by a second period of time—more than 24 hours of illumination (preferably about 10 μmol photons $m^{-2}$ $s^{-1}$ to about 250 μmol photons $m^{-2}$ $s^{-1}$). This procedure might be applied once or twice, or it might be applied several times in a repetitive manner.

The levels of gases such as oxygen, carbon dioxide, and ethylene can be controlled to favor alkaloid production or to favor biomass accumulation. Routine cultivation in lab scale cultivation vessels held in an atmosphere of air, with typical closures such as sheets, plugs, or caps result in dissolved oxygen levels below air saturation and levels of carbon dioxide and ethylene higher than that present in atmospheric air. Thus routinely, carbon dioxide levels in the head-space of the culture are typically greater than about 0.03% v/v. However, the concentrations of carbon dioxide and/or ethylene can be adjusted to favor alkaloid production or to favor cell propagation. In one embodiment, alkaloid production is favored by adjusting the carbon dioxide level in the head-space or aeration stream to be about 0.1% (approximately 3-times atmospheric) to about 10%, preferably about 0.3% to about 7% in equilibrium with the liquid at the temperature of operation. In another embodiment, ethylene is less than about 500 ppm and preferably less than 200 ppm as measured in the gas phase in equilibrium with the liquid phase at the temperature of operation. Gases can also be provided independently, e.g., the sources of oxygen and carbon dioxide can be different.

Dissolved gases can be controlled by varying one or more of: the agitation rate, the composition of aeration gas, the supply rate of the aeration gas, the venting rate of the aeration gas, and the total pressure in the cultivation vessel. Agitation rates can be controlled at about 1 to about 500 per minute (rotations or oscillations of agitators or circulations of fluid). The supply rate of gas can be any rate that is appropriate for achieving a dissolved gas concentration that is adequate or optimal for cell biomass accumulation or maintenance or product formation. Preferably, this rate is about 0.01 to about 10 volumes of gas per volume of culture broth per minute and can be supplied directly into the culture liquid, or into a separate portion of liquid that is subsequently mixed with the rest of the culture, or into the head space of the culture, or into a device for contacting the gas species with the culture medium. In one embodiment, dissolved oxygen concentrations are controlled at about 10% to about 200%, preferably about 20% to about 150%, of air saturation at the operating temperature. Of course, it is possible that for various operational reasons, e.g., temporary reduction in aeration, the dissolved oxygen level could be as low as zero for periods of time ranging from a few minutes to several hours. Specific useful combinations of oxygen, carbon dioxide, and ethylene, outside these ranges may be discovered through routine experimentation and are considered to be within the scope of this invention.

Cell Culture: Process Operations

The operating mode for a plant cell culture process refers to the way that nutrients, cells, and products are added or removed with respect to time (Payne et al. 1991). Ingredients provided to the cells can be provided in a number of different ways. Ingredients can be added in a particular stage of growth such as lag, exponential, or stationary. All ingredients can be provided at once and then after a suitable period of time, product can be recovered. Alternatively, not all ingredients can be provided all at once. Rather one or more of them can be provided at different times during the cultivation. Further, the additions can be discontinuous or staggered as to the time of initial contact and the duration of such provision can vary for different ingredients. Ingredients can be provided in a plurality of parts. One or more ingredients can be supplied as part of solutions separately contacted with the cell culture or portions thereof. Portions of the culture can be removed at any time or periodically and used for cryopreservation, further cell propagation, production, and/or recovery. Such cell-containing portions can be exposed further to nutrients or other ingredients as desired. Exemplary subculture procedures are described herein.

In one embodiment, medium containing nutrients or other ingredients can be added to replenish a portion or all of the removed volume. The replenishment (dilution) rate (volumetric rate of addition divided by the volume of liquid in the vessel) can vary between 0.1 times to 10 times the specific growth rate of the cells. Portions of such removed material can be added back into the original culture, for instance, cells and medium can be removed, a portion of the cells or medium can be used for product recovery and the remaining cells or medium can be returned. The supply rate of ingredients to the culture or levels of various ingredients in the culture can be controlled to advantageously produce and recover the product. Separate portions of the culture can be exposed to ingredients in any of the foregoing modes and then combined in proportions determined to be advantageous for production. Also the cell content of the culture can be adjusted to advantageously yield product or propagate cells. Adjustment of cell content can be advantageously combined with strategies for contacting with nutrients or other ingredients.

The culture method can include medium exchange. As documented for instance in Bringi WO 97/44476, the removal of spent medium and replenishment of fresh medium periodically, e.g., every few days, can significantly enhance total production, as well as increase the amounts of extracellular product. The stimulatory effects of medium exchange may be due to removal of product in situ, which would prevent feedback inhibition and product degradation. Such positive effects of in situ product removal on secondary metabolite production and secretion in suspension cultures of unrelated plants have been documented by, among others, Robins et al., "The Stimulation of Anthraquinone Production by Cinchona ledgeriana Cultures with Polymeric Adsorbents," Appl. Microbiol. Biotechnol. 24: 35-41 (1986) and Asada et al., "Stimulation of Ajmalicine Production and Excretion from *Catharanthus roseus*: Effects of Adsorption in situ, Elicitors and Alginate Immobilization," Appl. Microbial. Biotechnol. 30:475-81 (1989). The periodic removal of spent medium incorporates the above advantages, and additionally, may serve to de-repress secondary biosynthesis by removing other inhibitory components from the medium. In situ product removal can also be used without medium exchange. For example, the product can be removed by resin absorption to stimulate further production.

The replenishment of fresh medium to cells undergoing active biosynthesis may also enhance production by providing essential nutrients that have been depleted. For example, Miyasaka et al. were able to stimulate stationary phase cells of *Salvia miltiorhiza* to produce the diterpene metabolites cryptotanshinone and ferruginol simply by adding sucrose to the medium. Miyasaka et al., "Regulation of Ferruginol and Cryptotanshinone Biosynthesis in Cell Suspension Cultures of Salvia Miltiorrhiza," Phytochemistry 25: 637-640 (1986). Presumably, biosynthesis had ceased due to carbon limitation in the stationary phase. Using a periodic-medium-exchange protocol for the present culture method may provide similar benefits.

It is contemplated that the amount of medium exchanged, the frequency of exchange, and the composition of the medium being replenished can be varied in accordance with various embodiments of the invention. The ability to stimulate biosynthesis and secretion by medium exchange has important implications for the design and operation of an efficient commercial process in the continuous, semi-continuous, or fed-batch mode.

When all the nutrients are supplied initially, and the culture contents comprising cells and product are harvested at the end of the culture period, the operating mode is termed a "single-stage batch process." In practice, some ingredients could be added first and others shortly afterward for example, due to separate processing requirements for different ingredients. When a batch process is divided into two sequential phases, a growth and a production phase, with the medium being changed in between the two phases, the operating mode is termed a "two-stage growth/production batch process." The method can include a transition from growth medium to production medium by an abrupt stepwise change, or progressively by a series of steps, or by progressive, continuous change. In one extreme, the progressive change is accomplished by progressive replacement of media of incrementally changing composition. In another alternative, the progressive change is accomplished by feeding one or more components of the production medium into the growth phase culture. This is one example of the fed-batch process. In a "fed-batch" operation, particular medium components such as nutrients and/or one or more enhancement agents are supplied either periodically or continuously during all or part of the course of a one-stage or a two-stage culture. A description of nutrients and enhancement agents may be found, for instance, in Table A or Tables 1 and 2 of WO 97/44476. Additionally, a combination of abrupt and progressive changes can also be employed. In one example, some portion of the nutrient medium can be changed abruptly while other components are slowly fed.

Using a fed-batch mode, it has been found that cells can be sustained in a productive state for a prolonged period, and in fact, that productivity of the cells can be enhanced. It will be apparent to the skilled artisan, that the composition of the feed may be varied to obtain the desired results, such as extension of the production phase to increase product yield, or extension of the growth phase to achieve higher biomass density. Selection of suitable conditions to achieve optimum productivity and performance is easily within the skill of the ordinary artisan in view of the teachings described herein. Similarly, variations of other operating parameters, such as the timing and duration of the addition and the rate of the addition of the fed-batch components, to achieve the desired results, are within the reach of the skilled artisan in view of the teachings described herein.

In one embodiment, a substantial portion, but not all, of the contents of a batch culture is replaced by fresh medium for continued cell growth and production; this process mode resembles a "repeated draw and fill" operation and is termed a "semi-continuous process." In another embodiment, the process is "continuous," that is, fresh medium is continuously supplied, and effluent medium is continuously or repetitively removed.

In one embodiment, the operation mode is "perfusion mode," that is, cells are substantially retained within the reactor. In another embodiment, the process is "chemostat," that is, cells are continuously removed with the effluent medium.

Once initiated, a suspension culture can be further cultivated, either by separating the cells substantially from the medium (typically by filtration) and then reintroducing a portion to a medium containing nutrients, or by transferring a volume of culture broth (cells and medium) into a medium containing nutrients, or by allowing the cells to settle followed by removal of any portion of medium already present and reintroducing nutrient-containing medium. When cells are separated and transferred to a different nutrient-containing medium, the transferred amount can be about 0.3% to about 30%, preferably about 1% to about 25%, on a fresh weight basis. Note that as the cells acclimate and/or grow, this fraction may change. When cells and media are transferred volumetrically, the ratio of the transferred volume to the final volume can be from about 1% to substantially all of the volume. In this case, fresh nutrients can be supplied in a concentrated form, resulting in only a small volume increase. The culture can thus be divided into portions. In one embodiment, each portion is optionally used for alkaloid production. Each portion can, but need not, be cultured under the same conditions as one another or as the original culture. The culture duration is preferably 2-50 days, 2-15 days, 5-10 days, or about 7 days. The duration of growth can be extended by supplementing a partially depleted medium with nutrients.

Alkaloid Recovery

Alkaloids can be recovered from the entire culture or any portion of culture (medium only, cells only, or an amount of cells and medium together). Cell material can be lyophilised in advance to the extraction procedure. Other methods known in the art can be used in order to prepare cell material and/or medium for the appropriate extraction method. Alkaloids can be recovered by any method known in the art including, but not limited to, extraction using a non-aqueous polar solvent, extraction by using an acid medium, extraction by using a basic medium, recovery by resin absorption where the resin is either inside or outside of the culture vessel. Alkaloids can be recovered at any time during the cultivation or after the completion of the culture period.

Although particular features may be described with respect to particular embodiments, each feature can be used independently or in combination with any other feature described herein to increase the production of *Veratrum* alkaloids in cultures of Liliaceae. To further articulate the invention described above, we provide the following non-limiting examples.

EXAMPLES

Example 1

Cultivation of *Veratrum* Cells

*Veratrum* cell cultures are initiated from any suitable part of the *Veratrum* plant using accepted techniques of plant cell culture. Substantially undifferentiated cells are propagated on solidified or liquid nutrient medium under the following conditions, except that cells cultivated on solidified medium do not require agitation. *Veratrum* cells are cultivated at 20-30° C., at pH 4-7, in darkness, using agitation to mix the culture, and providing oxygen and other gases and ventilation by contacting oxygen-containing gas with the cell suspension. The oxygen is maintained at 10%-150% of air saturation at the operating temperature, and the carbon dioxide is maintained at higher than 0.05%. The level of oxygen and other gases is controlled by adjusting the agitation, pressure, composition of gas, ventilation rate, and/or feed rate of the gas.

The medium contains components capable of supporting *Veratrum* cell growth. For example, the medium can contain sugar (about 1-100 g/L) and cumulative nitrogen from one or more sources (about 1-100 mmol/L). The medium can also contain growth regulators such as auxin and/or cytokinin-like compounds, e.g., naphthalene acetic acid (NAA), phenoxyacetic acid and halogen substituted phenoxyacetic acids, picloram, dicamba, benzylaminopurine, kinetin, zeatin, thidiazuron, and/or indole acetic acid. The medium can optionally contain other *Veratrum* alkaloids, amino acids such as glutamine, a source of silver ion, e.g., silver nitrate or silver thiosulfate, or other ingredient capable of affecting ethylene biosynthesis or action. The inoculum concentration of *Veratrum* cells can be about 10 g fresh cell weight/L to about 300 g fresh cell weight/L. The medium can also contain one or more elicitors such as an indanoyl amide, a jasmonic acid-related substance, or another elicitor.

These medium components can be added at the beginning of the culture, after the exponential growth phase, or intermittently throughout the culture period. Medium components can be added at once or at different times during the cultivation and can be fed continuously or intermittently. The ingredients can be added either before or after the inclusion of plant cells in the culture broth. Further, nutrients or other ingredients can be added during cultivation. Optionally, the medium can be changed after a suitable period of cultivation whereby the cells are freshly exposed to a medium containing similar ingredients as described above. Such changes include changing the amount of one or more of sugars such as glucose, fructose, sucrose, and maltose, and/or changing the amount of one or more nitrogen sources such as nitrate, ammonium, amino acids, casamino acids.

After a period of cultivation, the culture is harvested and the levels of *Veratrum* alkaloids are quantified using high performance liquid chromatography (HPLC), and specific *Veratrum* alkaloids are identified using liquid chromatography-photodiode array-mass spectrometer (LC-PDA-MS). *Veratrum* alkaloids can be recovered from these cultures by appropriate extraction and purification procedures.

Example 2

Detection and Quantification of *Veratrum* Alkaloids

Figure 2B:
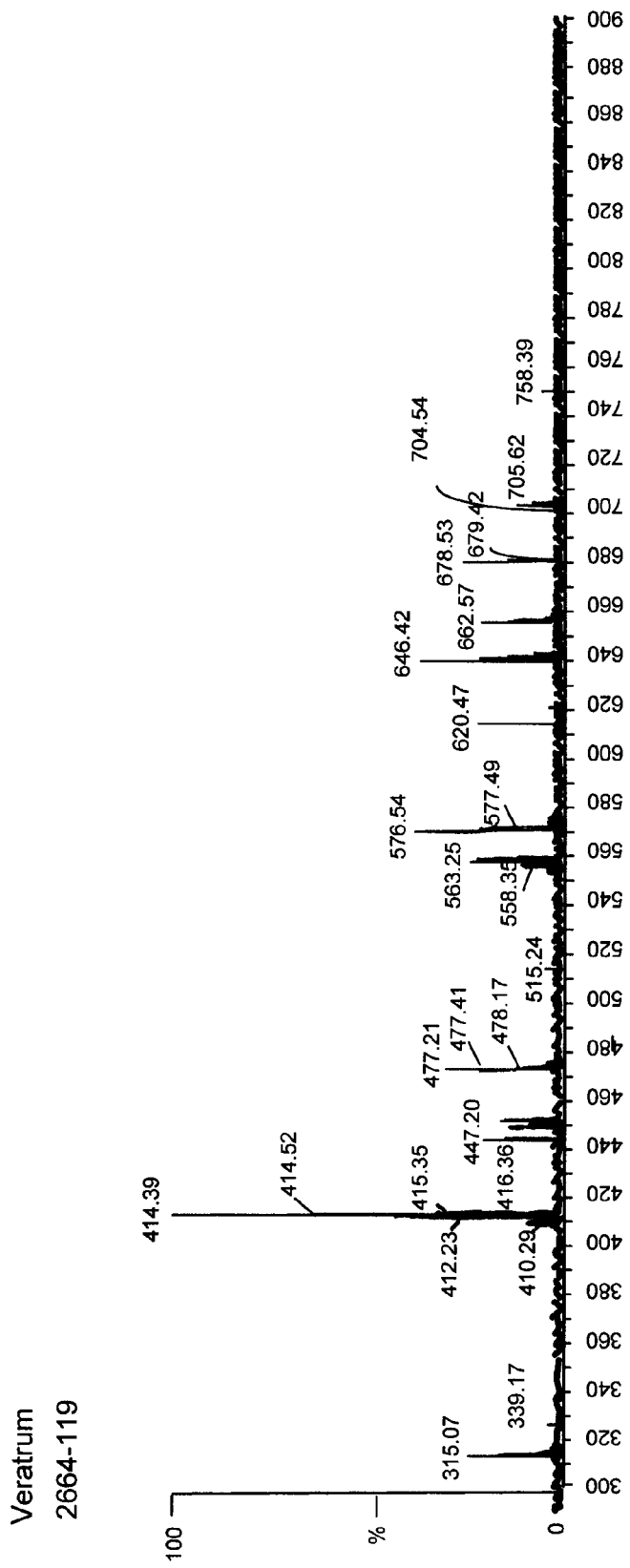
FIG. 2B shows MS spectrum of TIC peak at 3.40.

This example provides an appropriate analytical method for quantifying cyclopamine, jervine, and related steroidal alkaloids in *Veratrum* sp. cultures. The initial screening was performed by liquid chromatography-photodiode array-mass spectrometer (LC-PDA-MS). This technique is highly valuable in the identification of compounds in complex mixtures, especially when using some specialized mass spectrometric experiments like multiple reactions monitoring (MRM) and single ion monitor (SIM). This targeted approach is suitable for investigating the production of one or more target compounds in cell culture.

In the MRM experiments, Q1 scan (full scan, first quadrupole) and MSMS scan (fragment and productions are obtained) of an analyte is carried out. Then specific fragmentation products of the protonated pseudo-molecular ions ($M+H^+$) are selected, based on their initial scan. Instrument optimization is then performed to achieve a more sensitive detection based on the selected ion pairs. The selection method has proven to be accurate, precise, and sensitive at the μg/L level.

The MRM experiments using a triple quadrupole instrument were designed to obtain the maximum detection sensitivity for target compounds. This type of mass spectrometric experiment is widely used for detecting and quantifying drug and drug metabolites in the pharmaceutical industry.

Using the above techniques, it is possible to predict the precursor m/z and a fragment m/z (MRM transition) for many common metabolites of a drug molecule once the structure and molecular weight of the molecule are known. These MRM experiments can be used to screen for specific metabolites, and trigger a dependent product ion scan to confirm the metabolite structure. The same principle can be applied to study the production and optimization of target molecules in a cell culture if the molecular weight and structure of the target molecule are known. These highly sensitive MRM experiments were used to trigger dependent acquisitions of product ion scans (MS/MS). Cyclopamine and jervine were detected in *Veratrum* sp. plant cell cultures using this method.

General Methodology:

The following methodology was used for each Example, except where noted.

Equipment and Materials:

Reagents: acetonitrile (HPLC grade), methanol (HPLC grade), $CHCl_3$, and glacial acetic acid (all purchased from VWR)

Standards: Cyclopamine, jervine, and/or tomatidine (Calbiochem).

Equipment: Quattro Premier triple quadrupole mass spectrometer (Micromass Ltd.), Acquity HPLC system (Waters), BEH $C_{18}$ column (1.7 μm, 2.1×50 mm, Waters)

Standard Preparation 1 mg alkaloid (e.g., jervine, cyclopamine, tomatidine) was individually dissolved in acidic methanol (0.1% acetic acid v/v) to a final volume of 10 mL. The standard solution was sonicated for 1 min.

Sample Preparation:

Each *Veratrum* sample was crushed in a glass vial, and acidic methanol (20 mL, 1% formic acid) was added. The sample was sonicated for 2 hrs, then left in the dark overnight. The vial was centrifuged, and its supernatant removed. The supernatant was concentrated in a rotary evaporator, and the resulting extract was reconstituted in acidic methanol (1% formic acid v/v).

Liquid Chromatographic Separation:

Separation was performed on a Waters Acquity HPLC system equipped with a BEH $C_{18}$ column (1.7 μm, 2.1×50 mm). Twenty microliter (20 μL) aliquots were injected using an auto sampler. Solvent A was 0.05% formic acid in deionized water, and solvent B was HPLC grade acetonitrile with 0.05% formic acid.

Separation was achieved by an initial hold at 77% A for 1 minute, a linear gradient from 77% A to 100% B in 4.5 minutes, followed by holding at 100% B for 0.1 minute. During the analysis, the flow rate was 350 μL/min, and the column was kept at 35° C.

Mass Spectrometry:

All mass data was acquired on a Quattro Premier triple quadrupole mass spectrometer (Micromass Ltd.). The mass spectrometer was operated under MassLynx V4.0 software. For the samples investigated, the instrument was operated in positive mode electrospray with capillary voltage of 3.50 kV, a desolvation temperature of 120° C., a source temperature 120° C., and sample cone voltage of 45 V. (For the exemplary detection of cyclopamine and jervine, see Example 4, FIG. 3.)

Example 3

Production of Cyclopamine from Callus Culture

Seeds from *Veratrum californicum* were surface sterilized using standard techniques and cultivated on agar-solidified growth media. In some instances, the seeds were placed on water soaked filters for 1 to 3 months, then moved to water/agar (0.5-1% agar w/v) combination for 2 to 4 weeks. The growth media included:

MS salts, 2% w/v sucrose, and 10 micromol/L Picloram;

MS salts, 2% w/v sucrose, and 10 micromol/L Dicamba;

MS salts, 2% w/v sucrose, and 10 micromol/L alpha-naphthalene acetic acid (NAA).

Prior to initiation of suspension culture (described in Example 4), calli were initiated and then cultivated on solidified medium containing MS salts, 2% sucrose, and 10 μM Dicamba. Callus transfers were performed periodically about every 1-8 weeks depending on callus growth.

Approximately 50 mg samples of calli were crushed in a glass vial and extracted three times, each with 2 ml acidic methanol and $CHCl_3$ mixture (1:1 v/v) for 60 minutes in a sonicating bath. Each time, the vial was centrifuged and supernatant was removed. The combined supernatant was concentrated in a centrifuge evaporator (Genavac). The resulted extract was reconstituted in chloroform ($CHCl_3$) and methanol (MeOH) mixture to a final volume of 0.4 mL.

Chromatographic separation was achieved as described in Example 2 except we used an initial hold at 95% A for 1 minute, a linear gradient from 95% A to 100% B in 10 minutes, followed by holding at 100% B for 1 minute. The flow rate was 0.3 mL/min.

For the mass spectrometry analysis, each liquid stream was sampled for 0.1 s with mass spectra acquired from 150 to 1000 Da. The instrument was operated in positive mode electrospray with capillary voltage of 3.00 kV, a desolvation temperature of 120° C., a source temperature 100° C., and sample cone voltage of 45 V.

Cyclopamine was detected in both calli. See FIG. 1 and FIG. 2.

Example 4

Alkaloid Production from Suspension Culture

Suspension cultures were initiated by transferring about 1 g of callus material to a 125 ml Erlenmeyer flask containing 25 ml of a liquid growth medium containing MS salts, 2% sucrose, and 10 μM Dicamba. This suspension culture was maintained in the dark by shaking at 120 rpm on a 1'-throw shaker. The flasks were closed with an open cell silicone foam closure to allow for gas transfer. The flasks were maintained in an atmosphere of air. The suspension cells from callus were transferred 5 times at appropriate transfer intervals for a total of 45 days in liquid growth medium; the last cycle time was 11 days.

Suspension cells from four *Veratrum californicum* cultures were inoculated into MS-PM (a Murashige and Skoog Basal Salts-based production medium containing MS salts, macronutrients, micronutrients, vitamins, 5% sucrose, 100 μM methyl jasmonate (MJS), and 20 μM Dicamba) at a fresh weight inoculum concentration of 20% w/v. The cultures were incubated in an atmosphere of air, in the dark, at 25° C. and shaking at 180 rpm for 14 days.

Suspension cells were prepared for analysis according the general methodology (see Example 2), and the solvent from each 2 mL vial of reconstituted extract was removed by stream of nitrogen. The sample extracts were re-dissolved in 200 μL of acidic methanol (1% formic acid) before analysis.

Data acquisition was performed with full scan and Multiple Reaction Monitoring (MRM) of selected fragmentation products of the protonated pseudo-molecular ions (for cyclopamine m/z, M+H$^+$, 412.69→321.65 and for jervine 426.58→313.54). Appropriate four-point calibration curves were generated for each targeted compound of interest by injecting 20 μl of acidic MeOH (1% formic acid) solutions containing known amounts of cyclopamine and jervine.

Figure 3:
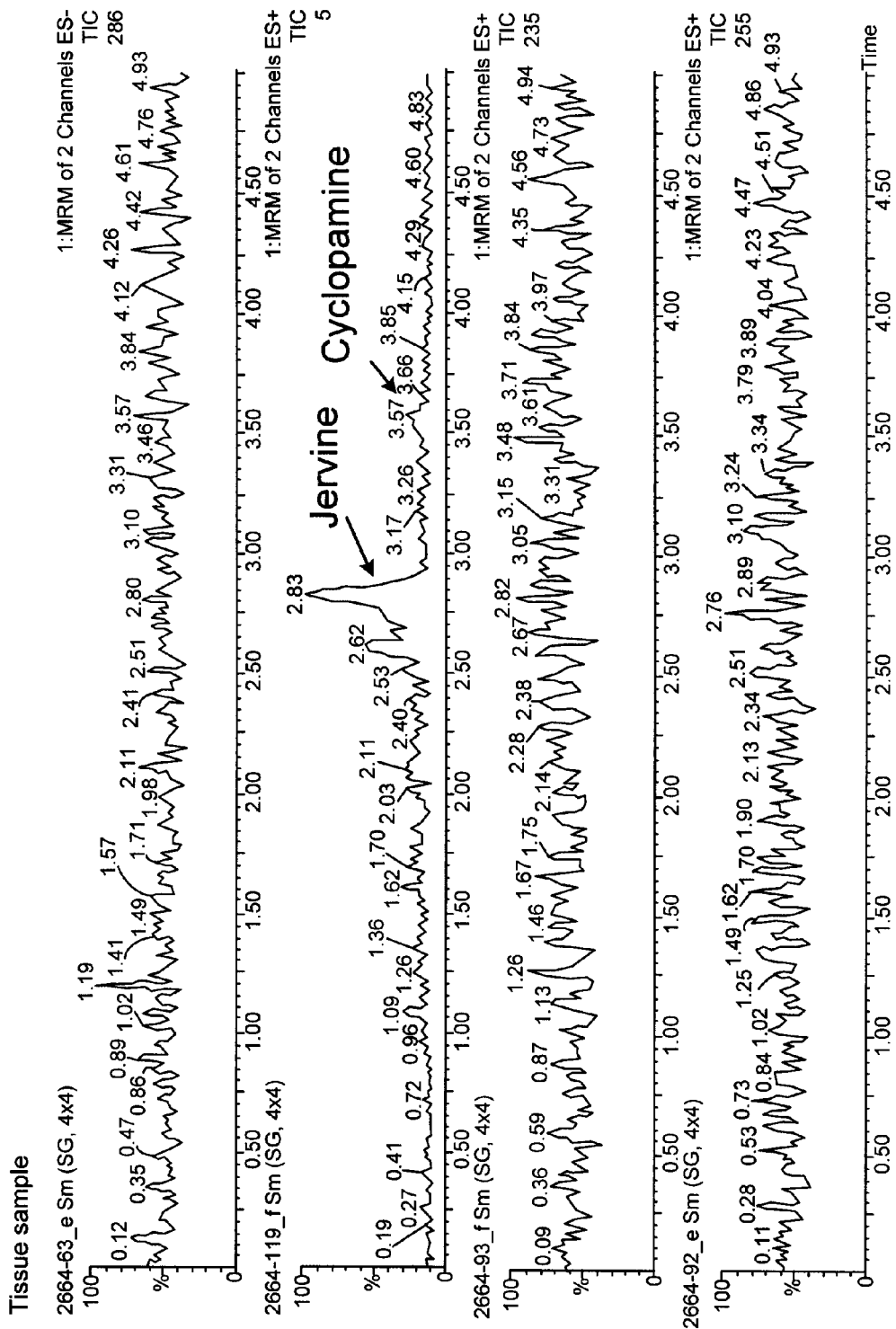
FIG. 3 shows the multiple reactions monitoring (MRM) spectra of *Veratrum* cell suspension samples. The ions for two analytes of interests were detected above the noise level: cyclopamine and jervine.
Figure 4:
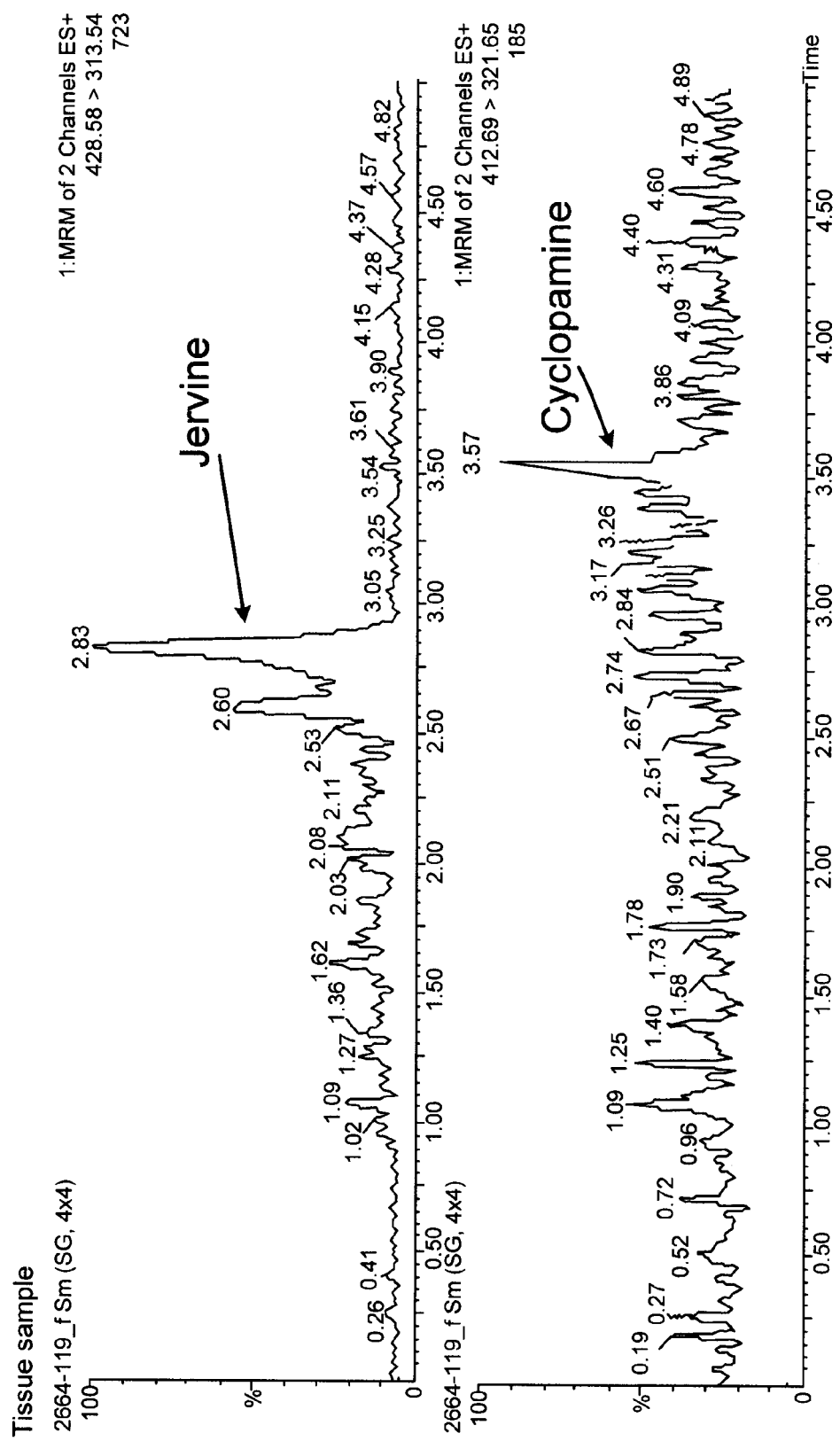
FIG. 4 shows the multiple reactions monitoring (MRM) spectra of a *Veratrum californicum* suspension culture by UPLC/MS/MS. The sample was concentrated before injection.

The identification of two alkaloids of interest—jervine and cyclopamine—was made by comparing their retention times, PDA UV spectra, MS spectra, and MS/MS spectra to those of known standards. Jervine and cyclopamine were detected in one cell culture (See FIG. 3 and FIG. 4). The concentration of cyclopamine in the extract was below the limit of quantification, but above the limit of detection (3:1, signal to noise ratio). Cyclopamine was detected at the μg/L level.

Example 5

Alkaloid Production from Suspension Culture

Seeds from *Veratrum californicum* were surface sterilized and embryos were extracted and placed on various solid media as described above in Example 3. After surface sterilization, these embryos were placed directly onto solid media containing SH salts, 2% w/v sucrose, and 10 μM Dicamba. Cultivation on solid media was continued until callus of undifferentiated cells was produced.

Figure 8:
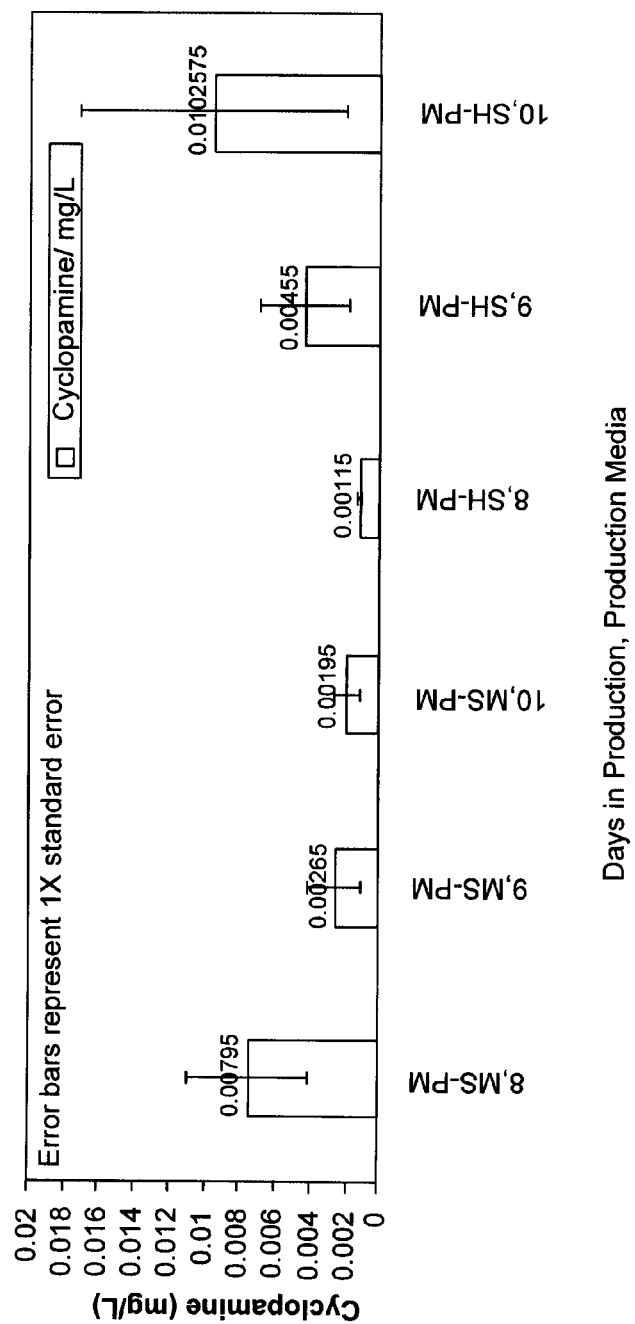
FIG. 8 shows cyclopamine titers in MS- and SH-based production medium on days 8, 9, and 10 using a *Veratrum californicum* suspension culture.
Figure 9:
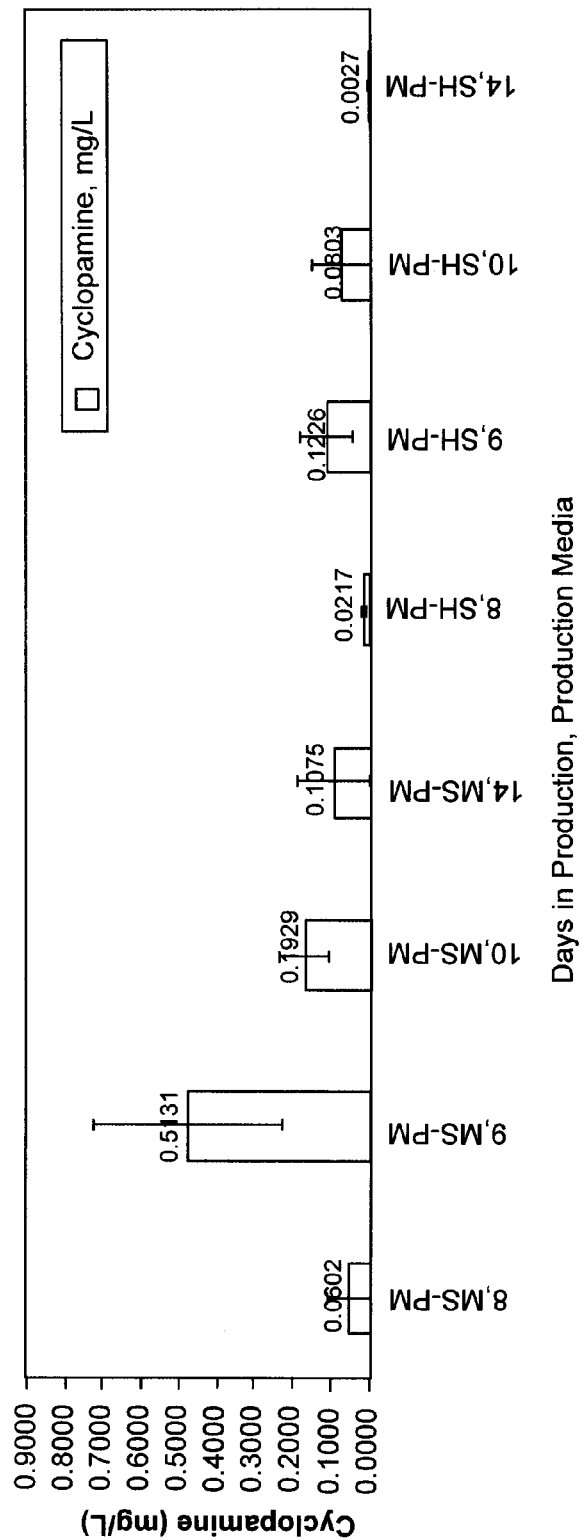
FIG. 9 shows cyclopamine titers in MS- and SH-based production medium on days 8, 9, and 10 using a *Veratrum californicum* suspension culture.

Portions of callus at a cell density of 5% (w/v) were placed in a liquid growth medium containing SH salts, 2% sucrose, and 10 μM Dicamba to form a suspension culture. The growth index for such suspension cultures was about 2 over a 7-day growth period. (Growth index is the ratio of the final fresh or dry weight to the corresponding initial fresh or dry weight over the duration of the culture period.) The cells were separated by filtration and then inoculated into MS-PM or SH-PM at a starting inoculation density of 20% w/v. Samples were incubated in an atmosphere of air at 85% humidity and 180 rpm in the dark at a temperature of 25° C. The cultures were sampled and analyzed after 8, 9, and 10 days of incubation. For one suspension cell culture of *Veratrum californicum*, *Veratrum* alkaloid production was highest at day 9 in both MS-PM and SH-PM. See FIG. 5A and FIG. 5B FIG. 6 and FIG. 7 show data from a repeated experiment using the same cell culture. Results for another suspension cell culture of *Veratrum californicum* are shown in FIG. 8 and FIG. 9.

Cyclopamine and jervine were detected in each sample. Alkaloid production increased from day 8 onwards, then later declined toward day 14.

Example 6

Cryopreservation of *Veratrum* Cells Using the Two-Step Method

*Veratrum califormicum* strain VEACCSP-94 undifferentiated cells are pre-cultured in liquid GM (IND64) media for about 7 days. Following pre-culturing, the undifferentiated cells are transferred to solid GM (IND-64) media plates comprising either about 0.8% or about 1.0% agarose.

Following pre-culturing, the *Veratrum* cells are transferred to liquid GM (IND-64) media comprising 0.3-0.5 M sorbitol and incubated at about 25° C. for about 24 hours. After incubation, the *Veratrum* cells are then transferred to liquid Cryopreservation 1 media and incubated for about 2-4 hours at between about 0° C. to 4° C.

The *Veratrum* cells are then cooled at a rate of about −0.33° C./minute until the cells are cooled to about −40° C. The cooled cells are immediately placed into liquid nitrogen and cryopreserved.

Example 7

Recovery of Thawed *Veratrum* Cells

The cryopreserved *Veratrum* cells of Example 6 are thawed from a frozen state in a 42° C. water bath with occasional stirring until the cells are no longer frozen. TTC cell viability tests are performed on the thawed cells to determine the cell viability of the thawed cells. TTC cell viability tests are well known to those of skill in the art. The TTC test reveal that greater than 50% of the thawed cells were viable.

Example 8

Cryopreservation Via Vitrification

Following pre-culturing of undifferentiated *Veratrum* plant cells on solid GM (IND64) media for a period of about 7 days as set forth previously herein, the plant cells are cryopreserved using vitrification techniques. The cultured *Veratrum* plant cells are transferred into liquid GM (IND64) media comprising about 0.5 M sorbitol, and the plant cells are cultured for about 32 hours on a rotary shaker (120 rpm). The transferred *Veratrum* suspension plant cells are small-aggregated plant cells produced using a Bellco homogenizer and a Bellco Cellector™ Tissue Sieve (20 mesh/860 um) (Bellco Biotechnology, Vineland, N.J.).

Next, the liquid GM (IND64) media is removed and the *Veratrum* plant cells are subsequently transferred into Cryopreservation 2 media. The composition of Cryopreservation 2 media is provided in Table 7.

TABLE 7

Cryopreservation 2 media
Components

Selected Sugar* [0.2 to 0.4M]
Selected Trisaccharide** [60 to 190 mM]
Permeating Agent [Ethylene Glycol 0.5 to 1M]

*By a selected sugar is intended a neutral sugar, an alcohol sugar, sucrose, maltose, trehalose or glycerol. Neutral sugars include but are not limited to glucose, arabinose, xylose, mannose, galactose, rhamnose or glucuronic acid. Alcohol sugars include but are not limited to malitiol, sorbitol, xylitol, isomalt, lactitol, erythritol or mannitol.
**By a selected trisaccharide is intended melezitose, panose, raffinose, kestose or lactosucrose.

The *Veratrum* plant cells are incubated in the Cryopreservation 2 media (cell density=20%) for about 3 hours at about 4° C. after which time the Cryopreservation 2 media is removed. About one part of the Cryopreservation 2 media-treated *Veratrum* plant cells are weighed and added into each cryo-vial. About 5 parts of Cold Cryoprotectant Solution is added into each cryo-vial and the cells are incubated at 0° C. (on ice) for a short period. The composition of Cold Cryoprotectant Solution is provided in Table 8. Immediately following this incubation, the cryo-vial is submerged in liquid nitrogen.

TABLE 8

Cold Cryoprotectant Solution
Components

Selected Sugar* [1.0-2.0M]
Divalent Cation [5.0-10.0 mM]
Permeating Agent [Ethylene Glycol 2-5M]

*By a selected sugar is intended a neutral sugar, an alcohol sugar, sucrose, maltose, trehalose or glycerol. Neutral sugars include but are not limited to glucose, arabinose, xylose, mannose, galactose, rhamnose or glucuronic acid. Alcohol sugars include but are not limited to malitiol, sorbitol, xylitol, isomalt, lactitol, erythritol or mannitol.

Cryovials comprising cryopreserved *Veratrum* plant cells are thawed following cryopreservation at a temperature of about 40° C., in a water bath or other sustained temperature environment, with occasional agitation or gentle stirring for about 4 minutes or until the frozen cells have thawed.

Following thawing and sterilization of the cryovials (typically by ethanol exposure), the contents of each thawed and sterilized cryo-vial is poured/diluted in 10 mls of liquid media containing about 5-10 mM divalent cations and 0.1-1.0 M sorbitol for 10 minutes, then passed through a suction filter to remove the solution, and the cells on the filter paper are transferred to solid GM (IND64) media and incubated at 25° C. in the dark for about 16 to about 24 hours. Then, the filter paper with cells is transferred to fresh solid GM (IND64) medium and then transferred every 7 days to fresh GM medium at 25° C. in the dark for restoration of cell functions.

The invention claimed is:

1. A method comprising:
   a) culturing undifferentiated plant cells of the family Liliaceae in a nutrient medium to form a cell culture that produces one or more *Veratrum* alkaloids, or a precursor of such an alkaloid or a mixture thereof; and
   b) recovering one or more alkaloids produced by culturing.

2. The method of claim 1, wherein the plant cells are *Veratrum* cells.

3. The method of claim 2, wherein the plant cells are *Veratrum californicum* cells.

4. The method of claim 1, wherein the plant cells are *Amianthium* cells.

5. The method of claim 1, wherein the alkaloid contains a C-nor-D-homo-[14(13→12)-abeo] ring.

6. The method of claim 1, wherein the alkaloid is cyclopamine.

7. The method of claim 1, wherein the alkaloid is jervine.

8. The method of claim 1, wherein the culturing step comprises culturing the plant cells in a growth medium, wherein the growth medium is capable of inducing a growth increase of at least 50% in one week.

9. The method of claim 1, wherein the culturing step comprises culturing the plant cells in a production medium, wherein the cell culture in production medium yields at least 0.1 mg/L of one or more alkaloids.

10. The method of claim 9, wherein the cell culture in production medium yields at least 0.3 mg/L of one or more alkaloids.

11. The method of claim 9, wherein the cell culture in production medium yields at least 0.5 mg/L of one or more alkaloids.

12. The method of claim 9, wherein the cell culture in production medium yields at least 0.75 mg/L of one or more alkaloids.

13. The method of claim 9, wherein the cell culture in production medium yields at least 1 mg/L of one or more alkaloids.

14. The method of claim 9, wherein the cell culture in production medium yields at least 1.5 mg/L of one or more alkaloids.

15. The method of claim 1, wherein the culturing step comprises:
   a) culturing the plant cells in a growth medium; and subsequently
   b) culturing the plant cells in a production medium that is different from the growth medium.

16. A method comprising:
   a) culturing undifferentiated plant cells of the genus *Veratrum* in a growth medium, wherein the growth medium is capable of inducing a growth increase of at least 50% in one week;
   b) culturing the undifferentiated plant cells in a production medium that is different from the growth medium, wherein the cells in production medium yield at least 0.1 mg/L of one or more *Veratrum* alkaloids, or precursors of such an alkaloid or mixtures thereof; and
   c) recovering at least one alkaloid produced by culturing.

17. A method of producing a C-nor-D-homo-[14(13→12)-abeo] ring containing alkaloid compound, said method comprising culturing undifferentiated cells of a plant belonging to the Liliaceae family which produce a C-nor-D-homo-[14(13→12)-abeo] ring containing alkaloid compound in a vessel in the presence of one or more stimulants which promote the biosynthesis of the C-nor-D-homo-[14(13→12)-abeo] ring containing alkaloid, wherein the gas phase in the culture vessel is controlled to less than the oxygen concentration in the atmosphere from the initial stage of the culture, or wherein the dissolved oxygen concentration in a fluid medium which is in contact with the cells is controlled to less than the saturated dissolved oxygen concentration at the temperature from the initial stage of the culture, and recovering C-nor-D-homo-[14(13→12)-abeo] ring containing alkaloid compound from the resulting cultures.

18. The method according to claim 17, wherein the cells of the plant which produce the C-nor-D-homo-[14(13→12)-abeo] ring containing alkaloid compound are cultured by introducing oxygenic gas containing 0.03%-10% of carbon dioxide into the culture vessel.

* * * * *